United States Patent
Short et al.

(10) Patent No.: US 11,865,110 B2
(45) Date of Patent: Jan. 9, 2024

(54) THROMBIN INHIBITORS, FORMULATIONS, AND USES THEREOF

(71) Applicant: VERSEON INTERNATIONAL CORPORATION, Dover, DE (US)

(72) Inventors: Kevin Michael Short, Fremont, CA (US); Maria de los Angeles Estiarte-Martinez, Fremont, CA (US); David Ben Kita, Fremont, CA (US); Nilantha Sudath Sirisoma, Fremont, CA (US)

(73) Assignee: Verseon International Corporation, Dover, DE (US)

( * ) Notice: Subject to any disclaimer, the term of this patent is extended or adjusted under 35 U.S.C. 154(b) by 415 days.

(21) Appl. No.: 17/259,108

(22) PCT Filed: Jul. 12, 2019

(86) PCT No.: PCT/US2019/041699
§ 371 (c)(1),
(2) Date: Jan. 8, 2021

(87) PCT Pub. No.: WO2020/014669
PCT Pub. Date: Jan. 16, 2020

(65) Prior Publication Data
US 2021/0315877 A1    Oct. 14, 2021

Related U.S. Application Data

(60) Provisional application No. 62/697,817, filed on Jul. 13, 2018.

(51) Int. Cl.
*A61K 31/4439* (2006.01)
*C07D 409/14* (2006.01)
*A61K 9/20* (2006.01)
*A61K 9/28* (2006.01)

(52) U.S. Cl.
CPC ........ *A61K 31/4439* (2013.01); *A61K 9/2095* (2013.01); *A61K 9/2846* (2013.01); *A61K 9/2893* (2013.01); *C07D 409/14* (2013.01)

(58) Field of Classification Search
CPC .............. A61K 31/4439; A61K 9/2095; A61K 9/2846; A61K 9/2893; C07D 409/14
USPC ......................................................... 514/341
See application file for complete search history.

(56) References Cited

FOREIGN PATENT DOCUMENTS

| WO | 2014145986 A1 | 9/2014 |
| WO | 2016044662 A1 | 3/2016 |

OTHER PUBLICATIONS

International Search Report and Written Opinion dated Sep. 20, 2019, Patent Application No. PCT/US2019/041699, filed Jul. 12, 2019, 14 pages.

*Primary Examiner* — Kristin A Vajda
(74) *Attorney, Agent, or Firm* — Norton Rose Fulbright US LLP

(57) ABSTRACT

Thrombin-inhibiting acylated pyrazole-pyridone compounds of formula (II) are disclosed herein, as well as pharmaceutical compositions, including tablets, that contain acylated pyrazole-pyridone compounds. These compounds are useful for the treatment and prevention of thrombin-related related diseases and disorders. Processes for making tablets containing acylated pyrazole-pyridones are also included.

(Structure II)

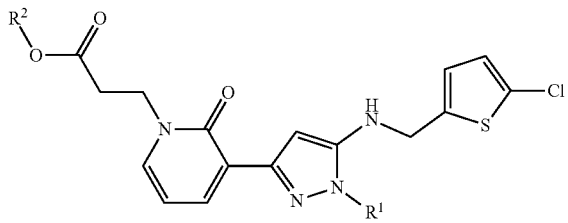

20 Claims, 4 Drawing Sheets

THROMBIN INHIBITORS, FORMULATIONS, AND USES THEREOF

CROSS-REFERENCE TO RELATED APPLICATIONS

The present application is a U.S. National Stage entry under 35 U.S.C. § 371 of International Application No. PCT/US2019/041699, filed on Jul. 12, 2019, designating the United States of America and published in English on Jan. 16, 2020, which in turn claims priority to U.S. Provisional Application No. 62/697,817, filed on Jul. 13, 2018, each of which is hereby incorporated by reference in its entirety.

FIELD OF THE INVENTION

The present disclosure generally relates to serine protease inhibitors, formulations, and uses thereof. The disclosure relates more particularly compounds, formulations, and methods for performing thrombin inhibition.

CROSS-REFERENCES TO PRIORITY AND RELATED APPLICATIONS

The present application claims the benefit of priority under 35 U.S.C. 119(e) to U.S. Provisional Application No. 62/697,817, THROMBIN INHIBITORS, FORMULATIONS, AND USES THEREOF, filed on Jul. 13, 2018, which is currently co-pending herewith and which is incorporated by reference in its entirety and for all purposes.

BACKGROUND

Serine proteases are a large family of enzymes with diverse biological functions, their commonality being the presence and critical function of the active-site serine residue. Their central function is the catalytic scission of peptide bond substrates via a Ser, His, Asp triad within the active site (Kraut, 1977 *J. Annual Review of Biochemistry,* 46:331-358).

Thrombin (fIIa, the active form of prothrombin) is a serine protease that is involved in the blood coagulation cascade, which is the system that deals with blood vessel injuries caused by bleeding events in mammalian systems. The cascade includes the Extrinsic and Intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor Xa is produced directly 'downstream' from the TF-fVIIa complex, and amplified manifold via the Intrinsic Pathway. FXa then serves as the catalyst for formation of thrombin (fIIa), which in turn activates platelets by the cleavage of protease-activated receptors and strengthens the clot by generating fibrin from fibrinogen. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated.

In disease states, undesired up- or down-regulation of any factor leads to conditions such as bleeding or thrombosis. Historically, anticoagulants have been used in patients at risk of suffering from thrombotic complications, such as angina, stroke and heart attack. Warfarin is a Vitamin K antagonist and inhibits factors II, VII, IX and X, amongst others. It does inhibit fibrinogenesis, but it has serious drug-drug interactions and its very long half-life (>2 days) can cause side effects which cannot be easily reversed. Additionally, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates antithrombin III (AT III), the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy.

The position of thrombin in the coagulation cascade has made it a popular target for drug discovery. Thrombin is a central protein in the coagulation process, which is activated and amplified upon vascular injury. Thrombin generation prompts a cascade in various factors in the coagulation cascade, ultimately depositing fibrin, the framework for a clot. The clot causes cessation of the bleeding event accompanying the vascular injury. Thrombin and associated proteins ultimately cause dissolution of the clot through 'fibrinolysis', returning the system back to the pre-injury state. In a 'normal' state of injury, this thrombin generation and clot deposition is desired. In a disease state, clot deposition is undesired. General thrombotic events are the clinical result of clot deposition and accumulation in the arteries, veins or within the heart. Eventual break-off of the accumulated clot structure into the vascular system can cause the clot to travel to the brain and/or lungs, resulting in a stroke, myocardial infarction (heart attack), pulmonary embolism, paralysis and consequent death. Compounds that inhibit thrombin have been shown in the literature to be useful as anticoagulants in vitro and in vivo, and such compounds can fulfill a critically unmet medical need for patients in the clinic.

A thorough discussion of thrombin and its roles in the coagulation process can be found in a variety of references, including the following which are incorporated herein by reference in their entireties and for all purposes: Wieland, H. A., et al., 2003, *Curr Opin Investig Drugs,* 4:264-71; Gross, P. L. & Weitz, J. I., 2008, *Arterioscler Thromb Vasc Biol,* 28:380-6; Hirsh, J., et al., 2005, Blood, 105:453-63; Prezelj, A., et al., 2007, *Curr Pharm Des,* 13:287-312. Without wishing to be bound by any theory, it is believed that the use of direct thrombin inhibitors (DTIs) is very well precedented, such as with the hirudin-based anticoagulants, and thus there is strong interest in the discovery and development of novel DTIs.

SUMMARY

The present invention encompasses compounds according to Structure I:

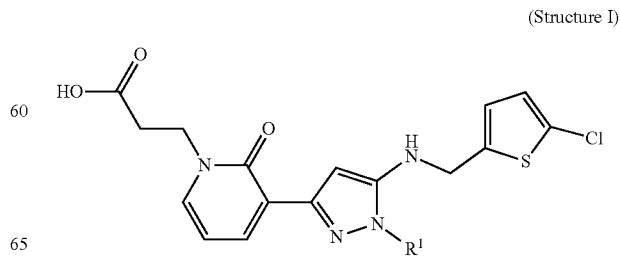

(Structure I)

and pharmaceutically acceptable salts, solvates, and cocrystals thereof, and uses thereof, wherein R¹ can be hydrogen or pivaloyl.

Embodiments of the invention include prodrugs of the compound according to claim 1 according to the general Structure II:

(Structure II)

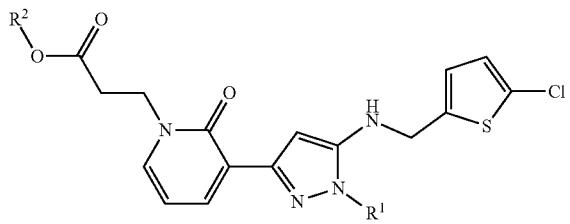

and pharmaceutically acceptable salts, solvates, and cocrystals thereof, wherein R¹ can be hydrogen and pivaloyl; and wherein R² can be substituted or unsubstituted alkyl or substituted or unsubstituted heteroalkyl. In some embodiments, R² can include the following groups:

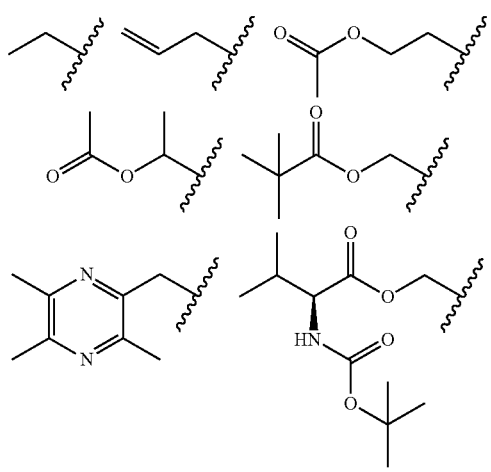

Further embodiments of the invention include compounds according to claim 1, wherein R¹ can be pivaloyl, as in Compound 1:

(Compound 1)

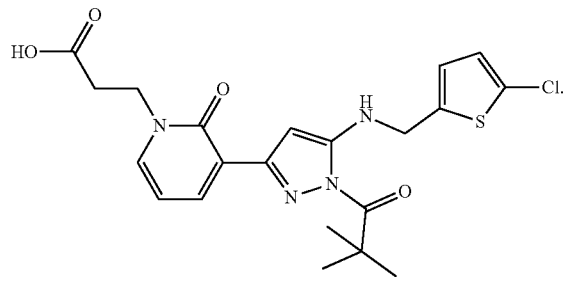

In some embodiments, the compound can be in crystalline form.

In some embodiments, wherein R¹ is pivaloyl, as in Compound 1, the crystalline form can have an x-ray powder diffraction pattern including at least five 2θ values selected from the group consisting of 9.9°, 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, wherein each of the at least five 2θ values can be within an error range of ±0.3°. In some embodiments, the crystalline form can have an x-ray powder diffraction pattern including at least five 2θ values selected from the group consisting of 4.9°, 9.7°, 14.4°, 16.0°, 16.5°, 17.0°, 18.2°, 18.5°, 19.2°, 19.7°, 20.2°, 22.8°, 23.3°, 24.0°, 24.5°, and 24.8°, wherein each of the at least five 2θ values can be within an error range of ±0.3°. In some embodiments, the crystalline form can have an x-ray powder diffraction pattern including at least five 2θ values selected from the group consisting of 8.6°, 9.5°, 11.8°, 12.4°, 12.9°, 14.2°, 15.2°, 15.5°, 16.5°, 17.2°, 18.8°, 19.1°, 20.1°, 20.9°, and 22.9°, wherein each of the at least five 2θ values can be within an error range of ±0.3°.

Embodiments of the invention also encompass the compound according to Structure I, wherein R¹ can be hydrogen, as in Compound 2:

(Compound 2)

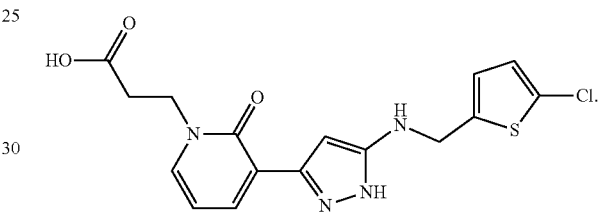

In some embodiments, the compound according to Structure I can be in the form of a pharmaceutically acceptable salt. In some embodiments, the pharmaceutically acceptable salt can have a counter-ion including potassium, calcium, L-arginine, L-lysine, meglumine, and/or tris(hydroxymethyl)aminomethane. In some embodiments, the counter-ion can be tris(hydroxymethyl)aminomethane. In some embodiments, the counter-ion can be tris(hydroxymethyl)aminomethane, and R¹ can be pivaloyl. In some embodiments, wherein the counter-ion can be tris(hydroxymethyl)aminomethane, and R¹ can be pivaloyl, the compound can be in crystalline form having an x-ray powder diffraction pattern including at least five 2θ values selected from the group consisting of 6.8°, 10.0°, 13.0°, 15.10, 16.0°, 16.5°, 18.0°, 18.4°, 19.8°, 20.5°, 20.8°, 21.2°, 21.5°, 22.8°, 23.3°, 25.9°, wherein each of the at least five 2θ values can be within an error range of ±0.3°.

In some embodiments, the compound or prodrug can be one of the following compounds:
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid;
3-[3-(5-{[(5-chlorothiophen-2-yl)methyl]amino}-1H-pyrazol-3-yl)-2-oxo-1,2-dihydropyridin-1-yl]propanoic acid;
2-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]acetic acid;
4-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]butanoic acid;
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]-2,2-difluoropropanoic acid;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propenamide;

1-(2-amino-2-methylpropyl)-3-(5-{[(5-chlorothiophen-2-yl)methyl]amino}-1-(furan-3-carbonyl)-1H-pyrazol-3-yl)-1,2-dihydropyridin-2-one;

3-[3-(5-{[(5-chlorothiophen-2-yl)methyl]amino}-1-(3-hydroxy-2,2-dimethylpropanoyl)-1H-pyrazol-3-yl)-2-oxo-1,2-dihydropyridin-1-yl]propanoic acid;

3-[3-(5-{[(5-chlorothiophen-2-yl)methyl]amino}-1-(2,2-dimethylbutanoyl)-1H-pyrazol-3-yl)-2-oxo-1,2-dihydropyridin-1-yl]propanoic acid;

3-[3-(5-{[(5-chlorothiophen-2-yl)methyl]amino}-1-(furan-3-carbonyl)-1H-pyrazol-3-yl)-2-oxo-1,2-dihydropyridin-1-yl]propanoic acid;

3-[3-(5-{[(5-chloro-1-oxo-1lambda4-thiophen-2-yl)methyl]amino}-1-(2,2-dimethylpropanoyl)-1H-pyrazol-3-yl)-2-oxo-1,2-dihydropyridin-1-yl]propanoic acid;

(2S,3S,4S,5R,6S)-6-({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)-3,4,5-trihydroxyoxane-2-carboxylic acid;

ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

prop-2-en-1-yl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate; 2-(acetyloxy)ethyl;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

1-(acetyloxy)ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl 2,2-dimethylpropanoate;

(3,5,6-trimethylpyrazin-2-yl)methyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl (2S)-2-{[(tert-butoxy)carbonyl]amino}-3-methylbutanoate;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl](2H4)propanoic acid;

3-{3-[5-({[5-chloro(3,4-2H2)thiophen-2-yl](2H2)methyl}amino)-1-(2,2-dimethylpropanoyl)-1H-pyrazol-3-yl]-2-oxo-1,2-dihydropyridin-1-yl}propanoic acid; and 3-[3-(5-{[(5-chlorothiophen-2-yl)(2H2)methyl]amino}-1-(2,2-dimethylpropanoyl)-1H-pyrazol-3-yl)-2-oxo-1,2-dihydropyridin-1-yl]propanoic acid.

Embodiments of the invention also encompass pharmaceutical compositions including one or more of any of the aforementioned compounds or prodrugs, or pharmaceutically acceptable salts, solvates, or cocrystals thereof, and one or more pharmaceutically acceptable excipients.

Embodiments of the invention also encompass methods for treating and/or preventing a disease or disorder in a subject, including administering one or more of any of the aforementioned compounds or prodrugs, or a pharmaceutical composition as described above, to a subject in need thereof in an amount effective to treat or prevent said disease or disorder.

In some embodiments of the methods, the disease or disorder can be a thrombotic disease or disorder and/or can involves a blood clot thrombus or the potential formation of a blood clot thrombus. In some embodiments, the thrombotic disease or disorder can include acute coronary syndrome, thromboembolism, and/or thrombosis. In some embodiments, the thromboembolism includes venous thromboembolism, arterial thromboembolism, and/or cardiogenic thromboembolism. In some embodiments, the venous thromboembolism includes deep vein thrombosis and/or pulmonary embolism. In some embodiments, the deep vein thrombosis and/or pulmonary embolism can occur following a medical procedure. In some embodiments, the thrombotic disease or disorder can involve dysfunctional coagulation or disseminated intravascular coagulation. In some embodiments, the subject can be undergoing percutaneous coronary intervention (PCI). In some embodiments, the thrombotic disease or disorder can involve a blood clot thrombus or the potential formation of a blood clot thrombus and can further involve stroke and/or one or more transient ischemic attacks (TIA). In some embodiments, the thrombotic disease or disorder involving a blood clot thrombus or the potential formation of a blood clot thrombus can further involve stroke, and the subject can have non-valvular atrial fibrillation.

In some embodiments, the thrombotic disease or disorder can involve a blood clot thrombus or the potential formation of a blood clot thrombus and can further involve pulmonary hypertension. In some embodiments, the pulmonary hypertension can be caused by one or more left heart disorder and/or chronic thromboembolic disease. In some embodiments, the pulmonary hypertension can be associated with one or more lung disease, including pulmonary fibrosis (idiopathic or otherwise), and/or hypoxia.

In some embodiments, the disease or disorder can include fibrosis, Alzheimer's Disease, multiple sclerosis, pain, cancer, inflammation, and/or Type I diabetes mellitus. In some embodiments, the disease or disorder can involve recurrent cardiac events after myocardial infarction.

In some embodiments, the venous thromboembolism can be associated with formation of a thrombus within a vein associated with one or more acquired or inherited risk factors and/or embolism of peripheral veins caused by a detached thrombus. In some embodiments, the one or more risk factors can include a previous venous thromboembolism.

In some embodiments, the cardiogenic thromboembolism can be due to formation of a thrombus in the heart associated with cardiac arrhythmia, heart valve defect, prosthetic heart valves or heart disease, and/or embolism of peripheral arteries caused by a detached thrombus. In some embodiments, the detached thrombus can be in the brain (ischemic stroke). In some embodiments, the detached thrombus can cause a transient ischemic attack (TIA). In some embodiments, the cardiogenic thromboembolism can be due to non-valvular atrial fibrillation.

In some embodiments, the thrombosis can be arterial thrombosis. In some embodiments, the arterial thrombosis can be due to one or more underlying atherosclerotic processes in the arteries. In some embodiments, the one or more underlying atherosclerotic processes in the arteries can obstruct or occlude an artery, cause myocardial ischemia (angina pectoris, acute coronary syndrome), cause myocardial infarction, obstruct or occlude a peripheral artery (ischemic peripheral artery disease), and/or obstruct or occlude an artery after a procedure on a blood vessel (reocclusion or restenosis after transluminal coronary angioplasty, reocclusion or restenosis after percutaneous transluminal angioplasty of periphery arteries).

In some embodiments, the treatment or prevention can include an adjunct therapy. In some embodiments, the subject can have myocardial infarction, and said adjunct therapy can be in conjunction with thrombolytic therapy. In some embodiments, the subject can have unstable angina pectoris, thrombosis, and/or heparin-induced thrombocytopenia, and said adjunct therapy can be in combination with antiplatelet therapy. In some embodiments, the subject can have non-valvular atrial fibrillation, and said adjunct therapy can be in conjunction with one or more other therapies. In some embodiments, the subject can have at least one of coronary artery disease and heart failure, and wherein said adjunct therapy can be in combination with antiplatelet therapy.

In some embodiments, the subject can further have valvular or non-valvular atrial fibrillation. In some embodiments, the subject can have valvular or non-valvular atrial fibrillation and can be undergoing percutaneous coronary intervention with a stent, and the adjunct therapy can be in combination with antiplatelet therapy.

Embodiments of the invention also encompass tablets including a pharmaceutical composition comprising Compound 1, wherein $R^1$ is pivaloyl.

In some embodiments, Compound 1 can exist as an amorphous solid in an amorphous solid dispersion. In some embodiments, the amorphous solid dispersion can be 50% of the tablet by weight. In some embodiments, the amorphous solid dispersion includes a first polymer. In some embodiments, the first polymer can be a vinylpyrrolidone-vinyl acetate copolymer. In some embodiments, Compound 1 and the first polymer are present in a weight ratio of 1:3.

In some embodiments, the tablets can include at least one disintegrant. In some embodiments, the disintegrant includes crospovidone. In some embodiments, the tablets can include at least one filler. In some embodiments, the filler includes microcrystalline cellulose or mannitol. In some embodiments, the tablets can include at least one lubricant or glidant. In some embodiments, the lubricant or glidant includes magnesium stearate or talc.

In some embodiments, the tablets can include an exterior layer or film. In some embodiments, the exterior layer or film includes at least a second polymer. In some embodiments, the second polymer can prevent dissolution of the tablet below pH 5.5. In some embodiments, the second polymer can be Eudragit® L 30 D-55. In some embodiments, the exterior layer or film includes 57% Eudragit® L 30 D-55, 14.6 Plasacryl® HTP20, and 28.4% water. In some embodiments, the second polymer is a methacrylic acid-ethyl acrylate copolymer.

In some embodiments, the tablets include an exterior layer of a second polymer, and wherein the tablet without said exterior layer can be 50% by weight the amorphous solid dispersion, 10% by weight crospovidone, 2% by weight magnesium stearate, 19% by weight microcrystalline cellulose, 18% by weight mannitol, and 1% by weight talc. In some embodiments, the second polymer can be Eudragit® L 30 D-55. In some embodiments, the tablet without the exterior layer has a total mass of 180 mg±9 mg. In some embodiments, the tablet without the exterior layer can have a total mass of 1000 mg±50 mg.

Embodiments of the invention also encompass tablets including a pharmaceutical composition including a prodrug having general Structure II, wherein $R^1$ can be hydrogen or pivaloyl, and wherein $R^2$ can be substituted or unsubstituted alkyl or substituted or unsubstituted heteroalkyl.

Embodiments of the invention also encompass processes of manufacturing the aforementioned tablets, wherein the process can include: (1) producing an amorphous solid dispersion of Compound 1; (2) granulating said amorphous solid dispersion of step (1) with intragranular raw materials in dry conditions; (3) blending said granules of step (2) with extragranular raw materials to form a final mixture; (4) compressing said final mixture of step (3) into a tablet; and (5) coating said tablet of step (4) with a film or layer. In some embodiments, the process can further include: (1) producing an amorphous solid dispersion of Compound 1 using a spray-dry dispersion (SDD) technique; (2) mixing said amorphous solid dispersion of step (1) with intragranular raw materials comprising at least one disintegrant and at least one lubricant; (3) dry granulating said mixture of step (2), wherein said granulation process comprises using a roller compactor to produce compacted ribbons, wherein said compacted ribbons are subsequently milled into granules; (4) blending the granules of step (3) with delumped extragranular raw materials comprising a disintegrant and a lubricant; (5) compressing the blend of step (4) into a tablet; and (6) coating said tablet of step (5) with a film or layer.

The following detailed description together with the accompanying drawings will provide a better understanding of the nature and advantages of the present invention.

BRIEF DESCRIPTION OF THE DRAWINGS

Those of skill in the art will understand that the drawings, described below, are for illustrative purposes only. The drawings are not intended to limit the scope of the present teachings in any way.

Various embodiments in accordance with the present disclosure will be described with reference to the drawings, in which.

DETAILED DESCRIPTION

Figure 1:
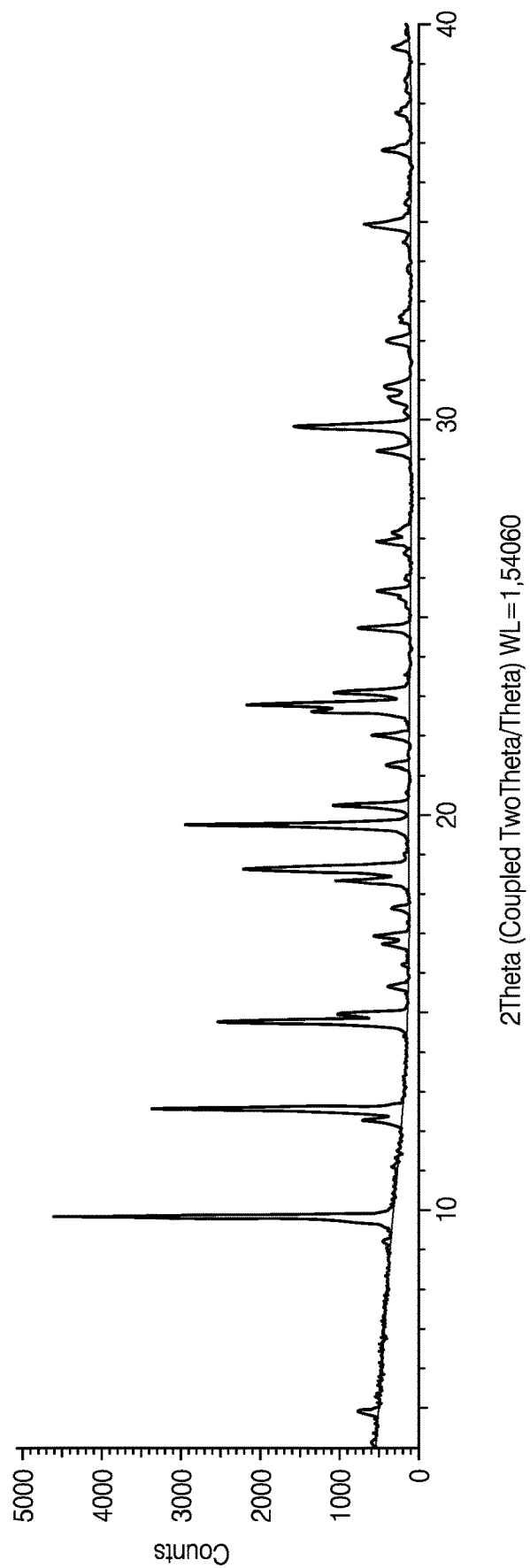
FIG. 1 shows an XRPD spectrum of a crystalline Form 1 of Compound 1.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques described and suggested herein include various aspects of the invention.

I. Definitions

Unless otherwise noted, terms are to be understood according to conventional usage by those of ordinary skill in the relevant art.

The abbreviations used herein have their conventional meaning within the chemical and biological arts. The chemical structures and formulas set forth herein are constructed according to the standard rules of chemical valency known in the chemical arts.

Where substituent groups are specified by their conventional chemical formulas, written from left to right, they equally encompass the chemically identical substituents that would result from writing the structure from right to left, e.g., —$CH_2O$— is equivalent to —$OCH_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "haloalkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which may be fully saturated, mono- or polyunsaturated, having the number of carbon atoms designated (i.e., $C_1$-$C_{10}$ means one to ten carbons). Examples of saturated hydrocarbon radicals include, but are not limited to, groups such as methyl, ethyl, propyl, butyl, pentyl, hexyl, and the like, including homologs and isomers of, for example, n-propyl, isopropyl, n-butyl, 1-methylpropyl (sec-butyl), 1,1-dimethylethyl (tert-butyl), and so forth, and the like. An unsaturated alkyl group is one having one or more double bonds or triple bonds. Examples of unsaturated alkyl groups include, but are not limited to, vinyl, 2-propenyl, crotyl, 2-isopentenyl, ethynyl, 1- and 3-propynyl, 3-butynyl, and the higher homologs and isomers. Accordingly, the term "alkyl" can refer to straight chain saturated, branched saturated, straight chain unsaturated, or branched unsaturated aliphatic hydrocarbon groups, and the like. Typically, an alkyl group will have from 1 to 24 carbon atoms, with those groups having 10 or fewer carbon atoms being preferred in the compounds disclosed herein. A "lower alkyl" is a shorter chain alkyl group, generally having eight or fewer carbon atoms.

The term "alkylene," by itself or as part of another substituent, means, unless otherwise stated, a divalent radical derived from a branched or unbranched, saturated or unsaturated alkyl, as defined above and as exemplified, but not limited by, —$CH_2$—, —$CH_2CH_2$—, —$CH_2CH_2CH_2$—, —$CH_2CH=CHCH_2$— and the like. Typically, an alkylene group will have from 1 to 24 carbon atoms, with those groups having 10 or fewer carbon atoms being preferred in the compounds disclosed herein. A "lower alkylene" is a shorter chain alkylene group, generally having eight or fewer carbon atoms.

The term "heteroalkyl," by itself or in combination with another term, means, unless otherwise stated, a straight or branched chain, or combinations thereof, consisting of at least one carbon atom and at least one heteroatom selected from the group consisting of O, N, Si, P, and S and wherein the nitrogen and sulfur atoms may optionally be oxidized, and the nitrogen heteroatom may optionally be quaternized. The heteroatom(s) O, N, Si, P, and S can be placed at any interior position of the chain. The heteroalkyl group can be fully saturated, mono- or polyunsaturated. Accordingly, the term "heteroalkyl" can refer to saturated or unsaturated, straight or branched chains, and the like. Examples include, but are not limited to: —$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)$_2$—$CH_3$, —CH=CH—O—$CH_3$, —$CH_2$—CH=N—$OCH_3$, —CN, and the like. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as defined above and as exemplified, but not limited by, —$CH_2$—$CH_2$—S—$CH_2$—$CH_2$— and —$CH_2$—S—$CH_2$—$CH_2$—NH—$CH_2$—, and the like. Further, for alkylene and heteroalkylene linking groups, no orientation of the linking group is implied by the direction in which the formula of the linking group is written. For example, the formula —$CO_2CH_2$— represents both —C(=O)$OCH_2$— and —$CH_2$OC(=O)—.

The terms "cycloalkyl," "cycloalkylene," "heterocycloalkyl," and "heterocycloalkylene," by themselves or in combination with other terms, mean, unless otherwise stated, cyclic versions of "alkyl," "alkylene, "heteroalkyl," and "heteroalkylene," respectively. The "cycloalkyl," "cycloalkylene," "heterocycloalkyl," and "heterocycloalkylene," groups include, for example, monocyclic rings having 3-8 ring members, as well as bicyclic rings having 4-16 ring members, tricyclic rings having 5-24 ring members, and so on. Examples of cycloalkyl include, but are not limited to, cyclopropyl, cyclobutyl, cyclopentyl, cyclohexyl, 1-cyclohexenyl, 3-cyclohexenyl, cycloheptyl, cyclooctyl, and the like. Examples of heterocycloalkyl include, but are not limited to, 1-(1,2,5,6-tetrahydropyridyl), 2-piperidinyl, 3-piperidinyl, 3-morpholinyl, tetrahydrofuran-2-yl, tetrahydrofuran-3-yl, tetrahydrothien-2-yl, tetrahydrothien-3-yl, 2-piperazinyl, and the like. A "cycloalkylene" and a "heterocycloalkylene," alone or as part of another substituent, means a divalent radical derived from a cycloalkyl and heterocycloalkyl, respectively.

The term "alkoxy" represents an alkyl group as defined above as having the indicated number of carbon atoms attached through an oxygen bridge. Examples include methoxy, ethoxy and the like. The term "alkyleneoxy," unless otherwise stated, represents a divalent alkoxy group. Examples of alkyleneoxy groups include —$OCH_2$—, $OCH_2CH_2$—, —OCH=$CHCH_2$—, and the like.

The term "alkylamino" represents one or two alkyl or heteroalkyl groups as defined above having the indicated number of carbon atoms attached through an amine bridge. Examples include dimethylamino, ethylamino, etc.) The two alkyl and/or heteroalkyl groups can be taken together with the nitrogen to which they are attached forming a cyclic system containing 3 to 8 carbon atoms with or without one $C_1$-$C_{16}$alkyl, aryl$C_0$-$C_{16}$alkyl, or $C_0$-$C_{16}$alkylaryl substituent. The term "alkyleneamino," unless otherwise stated, represents a divalent alkylamino group. Examples of alkyleneamino groups include —$NHCH_2$—, —$NHCH_2CH_2$—, —N($CH_3$)$CH_2CH_2$—, and the like.

The term "alkenyl" refers to a straight chain or branched unsaturated alkyl group. Double bonds may occur in any stable point along the chain and the carbon-carbon double bonds may have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, and the like. A "cycloalkenyl," alone or as part of another substituent, means a cyclic version of an alkenyl group. Examples of cycloalkenyl include cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds, wherein heteroalkyl is as defined above, and "heterocycloalkenyl" refers to a cyclic version of a heteroalkenyl group as defined above.

The term "alkynyl" refers to a straight chain or branched unsaturated alkyl group, having one or more triple bonds. The term "cycloalkynyl" refers to cycloalkyl, as defined above, additionally having one or more triple bonds. The term "heterocycloalkynyl" refers to heterocycloalkyl additionally having one or more triple bonds.

The term "acyl" refers, unless otherwise stated, to an alkyl group of the formula —C(O)R (alternatively depicted as —C(=O)R), where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that can be fused together (i.e., a fused ring aryl) or linked covalently, wherein each ring contains between 4-20 atoms, and preferably between 5-10 atoms. A fused ring aryl refers to multiple rings fused together wherein at least one of the fused rings is an aryl ring, and wherein each ring contains between 4-20 atoms, and preferably between 5-10 atoms. The term "heteroaryl" refers to aryl groups (or rings), as defined above, that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. Non-limiting examples of aryl and heteroaryl groups include phenyl, 1-naphthyl, 2-naphthyl, 4-biphenyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, 2,3-dihydro-1,4-benzodioxine, and the like. One of skill in the art will appreciate that in certain ring systems, one or more heteroatoms of a heteroaryl system can be optionally substituted (e.g. 1-pyrazoles).

An "arylene" and a "heteroarylene," alone or as part of another substituent, mean a divalent radical derived from an aryl and heteroaryl, respectively. Accordingly, the term "aryl" can represent an unsubstituted, mono-, di-, or tri-substituted monocyclic, polycyclic, biaryl and heterocyclic aromatic group covalently attached at any ring position capable of forming a stable covalent bond, certain preferred points of attachment being apparent to those skilled in the art (e. g. 3-indolyl, 4-imidazolyl).

For brevity, the term "aryl" when used in combination with other terms (e.g., aryloxy, arylthioxy, arylalkyl) includes both aryl and heteroaryl rings as defined above. Thus, the term "arylalkyl" and the like are meant to include those radicals in which an alkylene group links an aryl group to another portion of a molecule (e.g., benzyl, phenethyl, pyridylmethyl, and the like). Alkylene groups encompassed by the term "arylalkyl" include alkylene groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom.

The term "amido," unless otherwise stated, generally refers to the group —C(O)NR— wherein R is selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. No particular attachment orientation is implied by the term amido alone.

The term "carboxy," unless otherwise stated, generally refers to the group —C(O)O— or —CO$_2$—. No particular attachment orientation is implied by the term carboxy alone.

The term "oxo," as used herein, means an oxygen that is double bonded to a carbon atom.

Each of the above terms (e.g., "alkyl," "heteroalkyl," "aryl," "heteroaryl", etc.) includes both substituted and unsubstituted forms of the indicated radical.

Substituent groups for the substituted radicals are generally selected from the group consisting of, but not limited to, —OR', =O, =NR', =N—OR', —NR''''R'''', —SR', -halogen, —SiR'R''R''', —OC(O)R', —C(O)R', —CO$_2$R', —CONR''''R'''', —OC(O)NR''''R'''', —NR'C(O)R'', —NR'—C(O)NR''''R'''', —NR'C(O)$_2$R'', —NR'—C(NR''''R'''')=NR'', —S(O)R', —S(O)$_2$R', —S(O)$_2$NR''''R'''', —NR'SO$_2$R'', —CN, —NO$_2$, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylamido$C_{0-16}$alkyl, aryl$C_{1-16}$alkylamido$C_{0-16}$alkyl, —$C_{0-16}$alkylCOOR', —$C_{0-16}$alkylCONR''''R'''', wherein R', R'', R''', R'''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, optionally wherein R'''' and R'''' are taken together with the nitrogen to which they are attached forming a cyclic system containing 3 to 8 carbon atoms with or without one $C_{1-16}$alkyl, aryl$C_0$-$C_{16}$alkyl, or $C_0$-$C_{16}$alkylaryl substituent. Substituted alkyl, alkenyl, alkynyl, cycloalkyl, cycloalkenyl, heteroalkyl, heteroalkenyl, heterocycloalkyl, and heterocycloalkenyl groups can have any number of substituents from 0 to (2n+1) where n is the total number of carbon atoms in such radical. Substituted aryl and heteroaryl groups can have any number of substituents from 0 to the total number of valences on the ring system. Two substituents may optionally be joined to form alkylene or heteroalkylene groups. In one embodiment, the ring-forming substituents are attached to adjacent members of the base structure. For example, two ring-forming substituents attached to adjacent members of a cyclic base structure create a fused ring structure (e.g., 2-amino-3-ethyl benzene can be cyclized to form a 7-(2,3-dihydroindole) group). In another embodiment, the ring-forming substituents are attached to a single member of the base structure. For example, two ring-forming substituents attached to a single member of a cyclic base structure create a spirocyclic structure (e.g., 2-(hydroxymethyl)-2-methyl-cyclohexane can be cyclized to form a 2-oxaspiro[3.5]nonane group). In yet another embodiment, the ring-forming substituents are attached to non-adjacent members of the base structure. For example, two ring-forming substituents attached to non-adjacent members of a cyclic base structure create a bridged cyclic structure (e.g., 1-aminocyclooctane can be cyclized to form 9-aza-[3.3.1]bicyclononane).

The term "about" used in the context of a numeric value indicates a range of +/−10% of the numeric value, unless expressly indicated otherwise.

II. Compounds

The present disclosure relates to substituted acylated pyrazole-pyridone compounds. These compounds exhibit biological activity, such as inhibitory activity against thrombin, which is a serine protease.

Embodiments of the invention encompass compounds with the following Structure I:

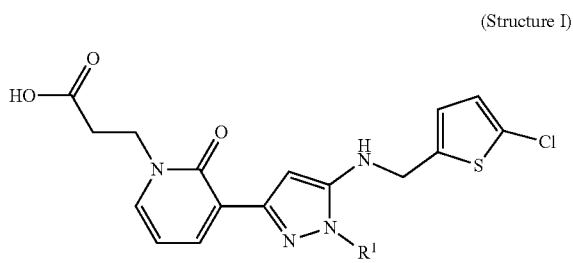

(Structure I)

or pharmaceutically acceptable salt, solvate, or cocrystal thereof, wherein $R^1$ is selected from the group consisting of hydrogen and pivaloyl, which describes the formula —C(O)C(CH$_3$)$_3$ as depicted below:

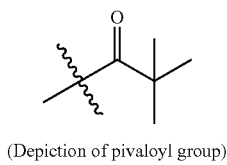 [SMILES: *C(=O)C(C)(C)C]

(Depiction of pivaloyl group)

In some embodiments, $R^1$ is pivaloyl, resulting in 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid, as shown below as compound 1:

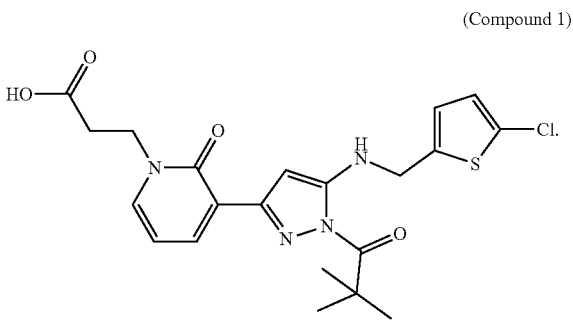 [SMILES: CC(C)(C)C(=O)n1nc(-c2cccn(CCC(=O)O)c2=O)cc1NCc1ccc(Cl)s1]

(Compound 1)

Figure 2:
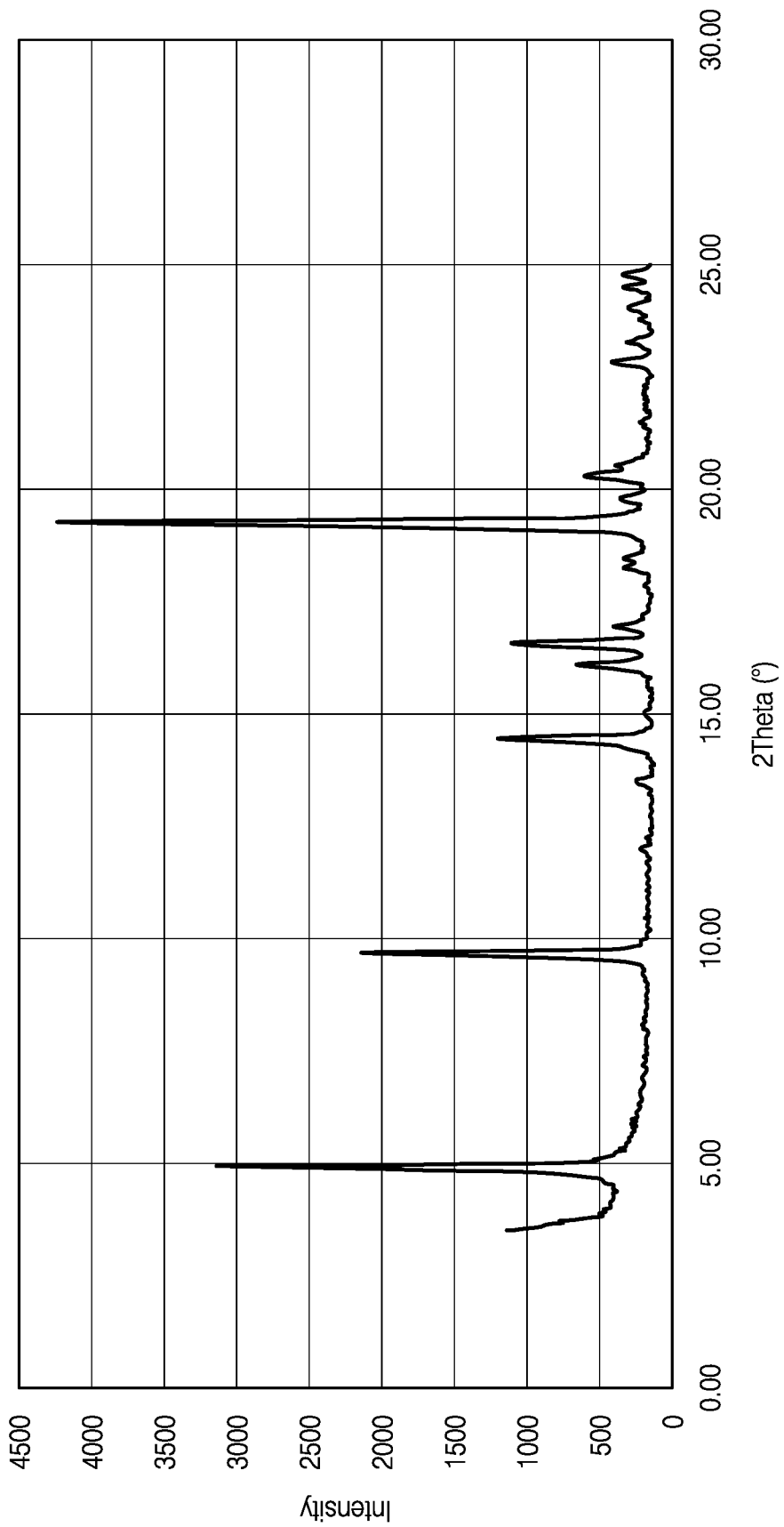
FIG. 2 shows an XRPD spectrum of a crystalline Form 2 of Compound 1.
Figure 3:
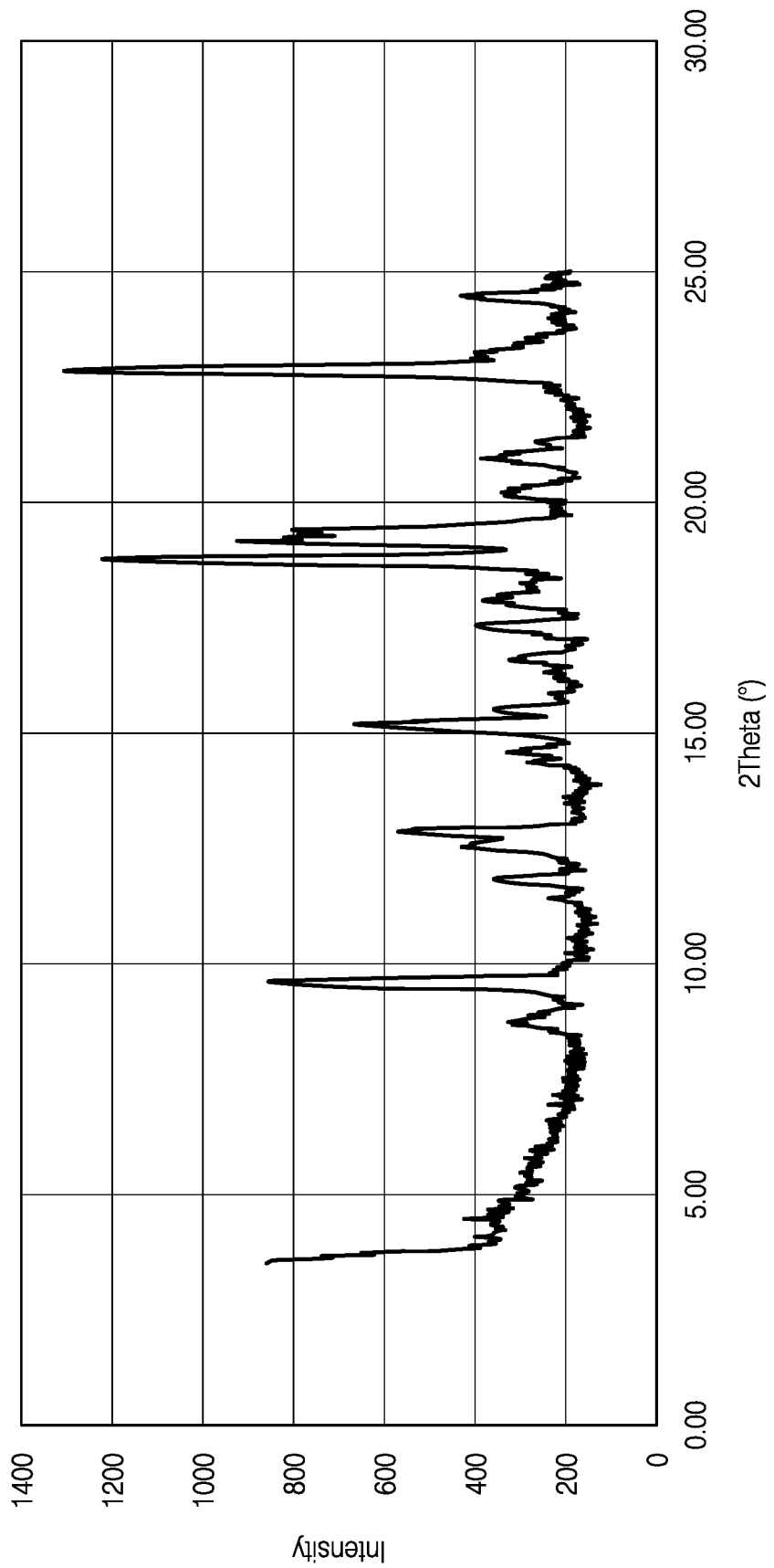
FIG. 3 shows an XRPD spectrum of a crystalline Form 3 of Compound 1.

In some embodiments, Compound 1 exists in crystalline form. In one embodiment, the crystalline form has an x-ray powder diffraction pattern comprising a selection of one, two, three, four, five, or more 2θ values selected from the group consisting of 9.9°, 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, each within an error range of ±0.3°, as shown in FIG. 1 as crystal Form 1. In another embodiment, the crystalline form has an x-ray powder diffraction pattern comprising a selection of one, two, three, four, five, or more 2θ values selected from the group consisting of 4.9°, 9.7°, 14.4°, 16.0°, 16.5°, 17.0°, 18.2°, 18.5°, 19.2°, 19.7°, 20.2°, 22.8°, 23.3°, 24.0°, 24.5°, and 24.8°, each within an error range of ±0.3°, as shown in FIG. 2 as crystal Form 2. In another embodiment, the crystalline form has an x-ray powder diffraction pattern comprising a selection of one, two, three, four, five, or more 2θ values selected from the group consisting of 8.6°, 9.5°, 11.8°, 12.4°, 12.9°, 14.2°, 15.2°, 15.5°, 16.5°, 17.2°, 18.8°, 19.1°, 20.1°, 20.9°, and 22.9°, each within an error range of ±0.3°, as shown in FIG. 3 as crystal Form 3.

In some embodiments, $R^1$ is hydrogen, resulting in 3-[3-(5-{[(5-chlorothiophen-2-yl)methyl]amino}-1H-pyrazol-3-yl)-2-oxo-1,2-dihydropyridin-1-yl]propanoic acid, as shown below as compound 2:

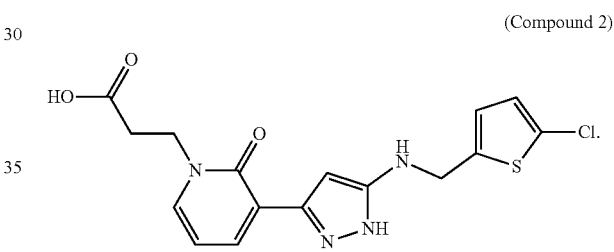

(Compound 2)

Additional embodiments include salt forms of compounds encompassed by structure I, including Compound 1. In these embodiments, the compound exists in a charged state with a counter-ion. In some embodiments, the counter-ion can be selected from the group consisting of sodium, potassium, calcium, L-arginine, L-lysine, meglumine, and tris(hydroxymethyl)aminomethane.

Figure 4:
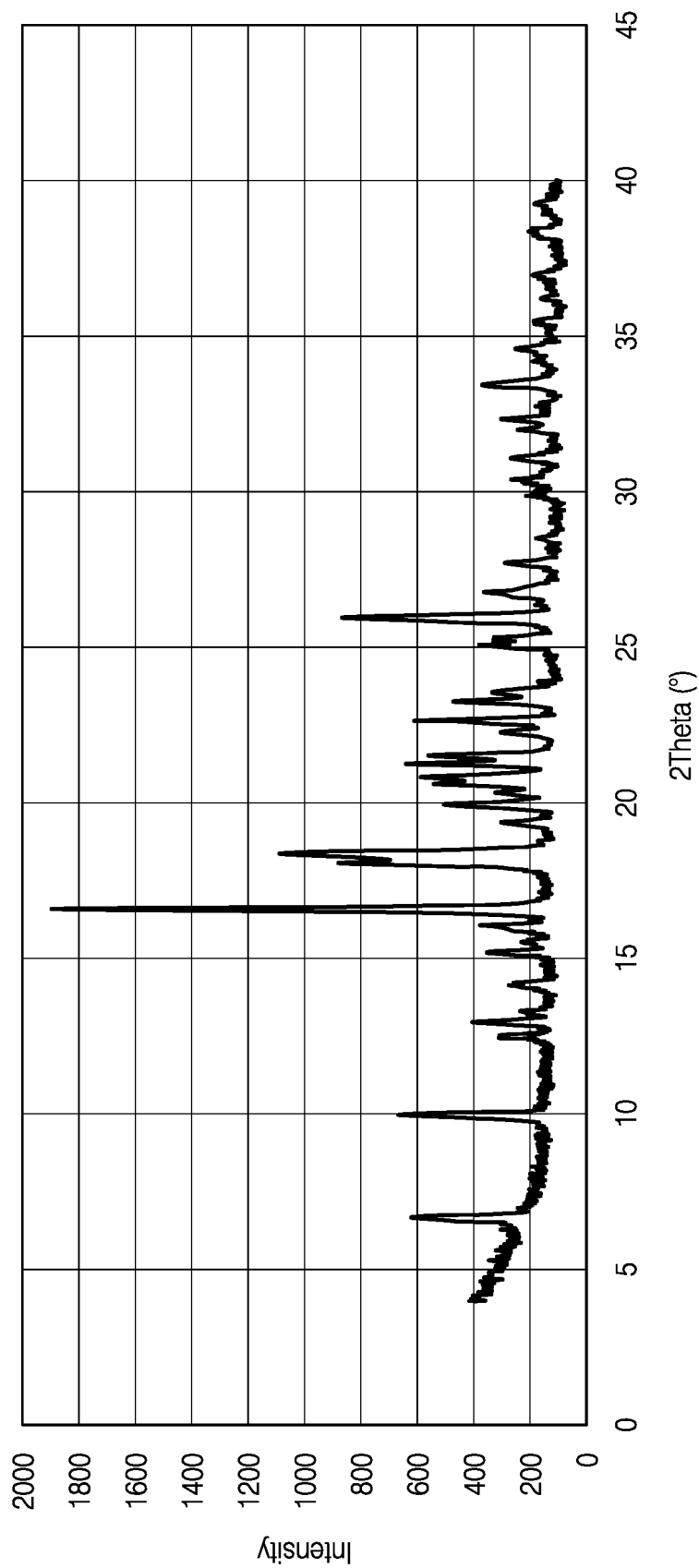
FIG. 4 shows an XRPD spectrum of a crystalline Form 4 of Compound 1 as a salt with tris(hydroxymethyl)aminomethane.

In some embodiments when Compound 1 is in a salt form having tris(hydroxymethyl)aminomethane as a counter-ion, the substance is in crystalline form. In some embodiments, the crystalline form of Compound 1 in a salt form having tris(hydroxymethyl)aminomethane as a counter-ion has an x-ray powder diffraction pattern comprising a selection of one, two, three, four, five, or more 2θ values selected from the group consisting of 6.8°, 10.0°, 13.0°, 15.1°, 16.0°, 16.5°, 18.0°, 18.4°, 19.8°, 20.5°, 20.8°, 21.2°, 21.5°, 22.8°, 23.3°, and 25.9°, each within an error range of ±0.3°, as shown in FIG. 4 as crystal Form 4.

Certain embodiments of the invention relate to certain prodrugs of Structure I, which have the general formula of Structure II:

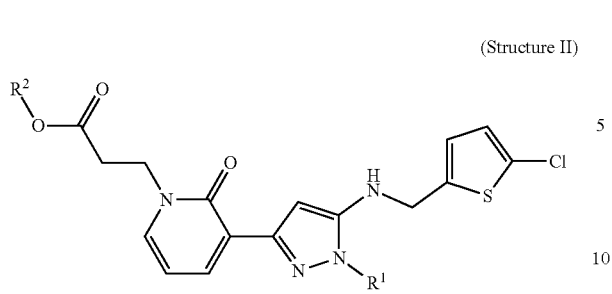

(Structure II)

Wherein R¹ is selected from the list consisting of hydrogen and pivaloyl, and R² is selected from the list of substituted or unsubstituted alkyl and substituted or unsubstituted heteroalkyl. In further embodiments, R² is selected from a list consisting of the following structures:

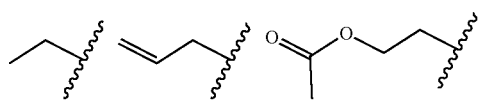

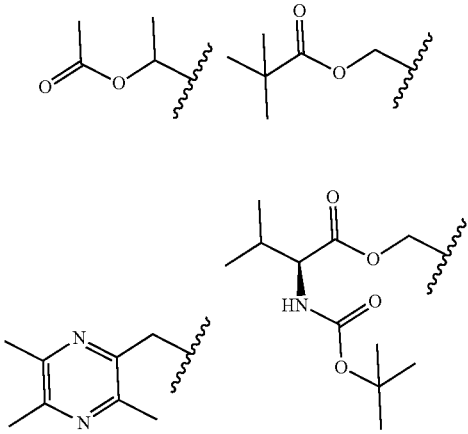

In some embodiments, prodrugs of Structure I can be formulated as pharmaceutically acceptable salts, solvates, and cocrystals thereof.

Additional compounds disclosed herein include the following compounds listed in Table A, below:

TABLE A

| Comp. No. | IUPAC Name | Structure |
|---|---|---|
| 3 | 2-[3-(5-{[(5-chlorothiophen-2-yl)methyl]amino}-1H-pyrazol-3-yl)-2-oxo-1,2-dihydropyridin-1-yl]acetic acid | 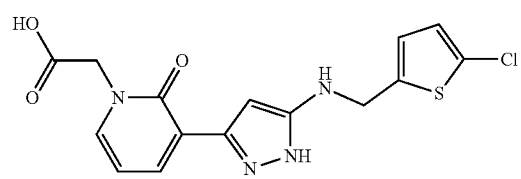 [SMILES: O=C(O)Cn1cccc(-c2cc(NCc3ccc(Cl)s3)[nH]n2)c1=O] |
| 4 | 2-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]acetic acid | 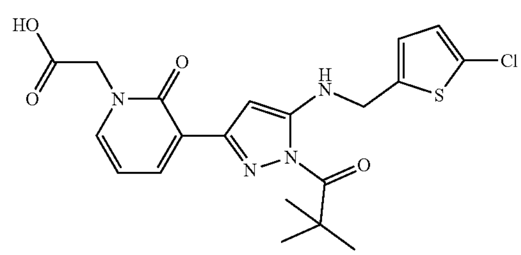 [SMILES: CC(C)(C)C(=O)n1nc(-c2cccn(CC(=O)O)c2=O)cc1NCc1ccc(Cl)s1] |
| 5 | 4-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]butanoic acid | 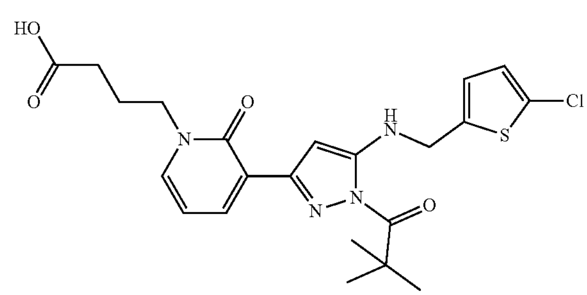 [SMILES: CC(C)(C)C(=O)n1nc(-c2cccn(CCCC(=O)O)c2=O)cc1NCc1ccc(Cl)s1] |

TABLE A-continued

| Comp. No. | IUPAC Name |
|---|---|
| 6 | 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]-2,2-difluoropropanoic acid |
| 7 | 3-(5-{[(5-chlorothiophen-2-yl)methyl]amino}-1-(2,2-dimethylpropanoyl)-1H-pyrazol-3-yl)-1-(2-methoxyethyl)-1,2-dihydropyridin-2-one |
| 8 | 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanamide |
| 9 | 1-(2-amino-2-methylpropyl)-3-(5-{[(5-chlorothiophen-2-yl)methyl]amino}-1-(furan-3-carbonyl)-1H-pyrazol-3-yl)-1,2-dihydropyridin-2-one |
| 10 | 3-[3-(5-{[(5-chlorothiophen-2-yl)methyl]amino}-1-(3-hydroxy-2,2-dimethylpropanoyl)-1H-pyrazol-3-yl)-2-oxo-1,2-dihydropyridin-1-yl]propanoic acid |

TABLE A-continued

| Comp. No. | IUPAC Name | Structure |
|---|---|---|
| 11 | 3-[3-(5-{[(5-chlorothiophen-2-yl)methyl]amino}-1-(2,2-dimethylbutanoyl)-1H-pyrazol-3-yl)-2-oxo-1,2-dihydropyridin-1-yl]propanoic acid | 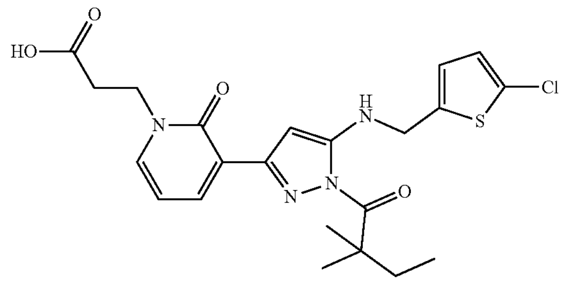 [SMILES: CCC(C)(C)C(=O)n1nc(-c2cccn(CCC(=O)O)c2=O)cc1NCc1ccc(Cl)s1] |
| 12 | 3-[3-(5-{[(5-chlorothiophen-2-yl)methyl]amino}-1-(furan-3-carbonyl)-1H-pyrazol-3-yl)-2-oxo-1,2-dihydropyridin-1-yl]propanoic acid | 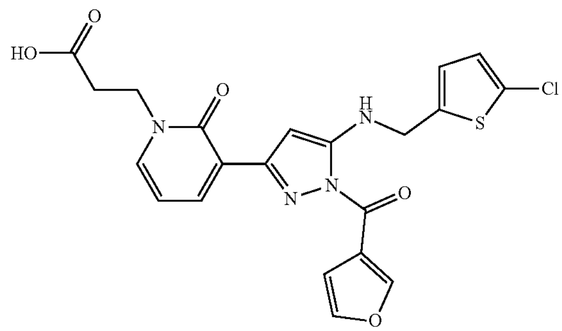 [SMILES: O=C(O)CCn1cccc(-c2cc(NCc3ccc(Cl)s3)n(C(=O)c3ccoc3)n2)c1=O] |
| 13 | 3-[3-(5-{[(5-chloro-1-oxo-1lambda4-thiophen-2-yl)methyl]amino}-1-(2,2-dimethylpropanoyl)-1H-pyrazol-3-yl)-2-oxo-1,2-dihydropyridin-1-yl]propanoic acid | 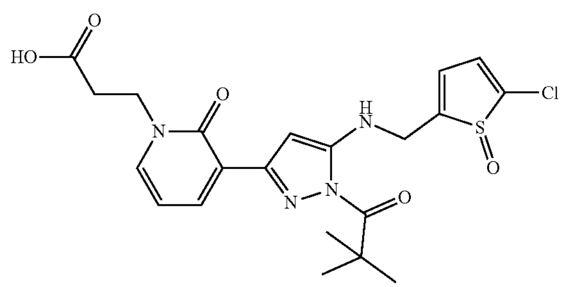 [SMILES: CC(C)(C)C(=O)n1nc(-c2cccn(CCC(=O)O)c2=O)cc1NCC1=CC=C(Cl)S1=O] |
| 14 | (2S,3S,4S,5R,6S)-6-({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)-3,4,5-trihydroxyoxane-2-carboxylic acid | 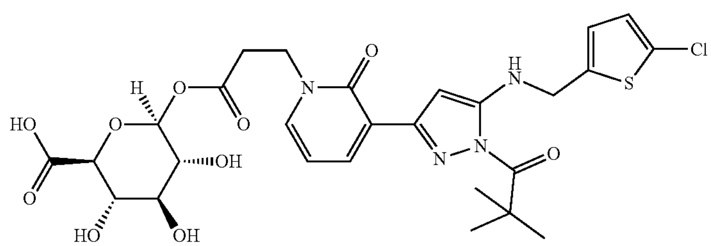 [SMILES: CC(C)(C)C(=O)n1nc(-c2cccn(CCC(=O)O[C@@H]3O[C@H](C(=O)O)[C@@H](O)[C@H](O)[C@H]3O)c2=O)cc1NCc1ccc(Cl)s1] |
| 15 | ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate | 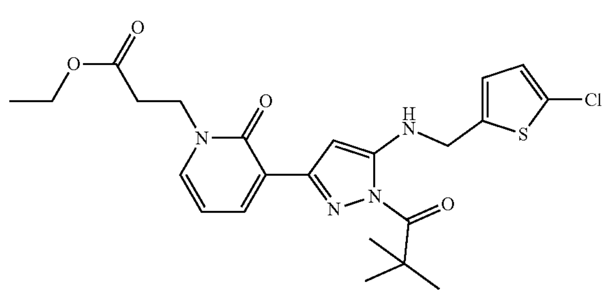 [SMILES: CCOC(=O)CCn1cccc(-c2cc(NCc3ccc(Cl)s3)n(C(=O)C(C)(C)C)n2)c1=O] |

TABLE A-continued

| Comp. No. | IUPAC Name |
|---|---|
| 16 | prop-2-en-1-yl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate |
| 17 | 2-(acetyloxy)ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate |
| 18 | 1-(acetyloxy)ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate |
| 19 | ({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl 2,2-dimethylpropanoate |
| 20 | (3,5,6-trimethylpyrazin-2-yl)methyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate |

TABLE A-continued

| Comp. No. | IUPAC Name | Structure |
|---|---|---|
| 21 | ({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl (2S)-2-{[(tert-butoxy)carbonyl]amino}-3-methylbutanoate | 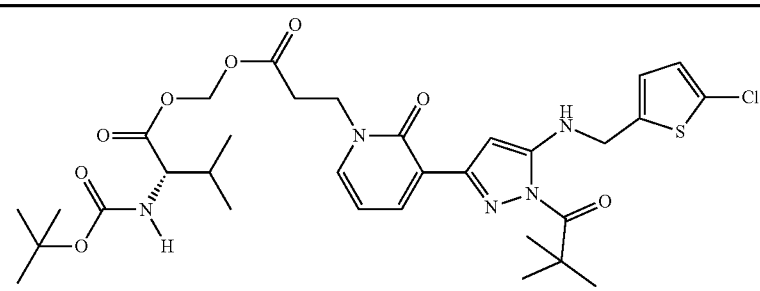 |
| 22 | 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl](2H4)propanoic acid | 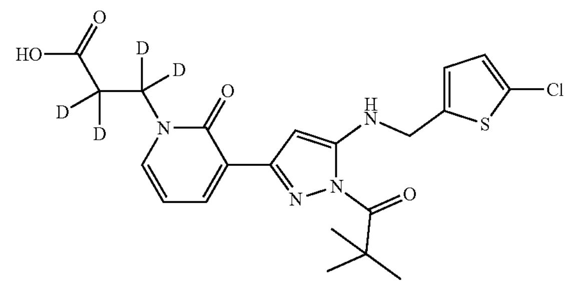 [SMILES: [2H]C([2H])(C(=O)O)C([2H])([2H])n1cccc(-c2cc(NCc3ccc(Cl)s3)n(C(=O)C(C)(C)C)n2)c1=O] |
| 23 | 3-{3-[5-({[5-chloro(3,4-2H2)thiophen-2-yl](2H2)methyl}amino)-1-(2,2-dimethylpropanoyl)-1H-pyrazol-3-yl]-2-oxo-1,2-dihydropyridin-1-yl}propanoic acid | 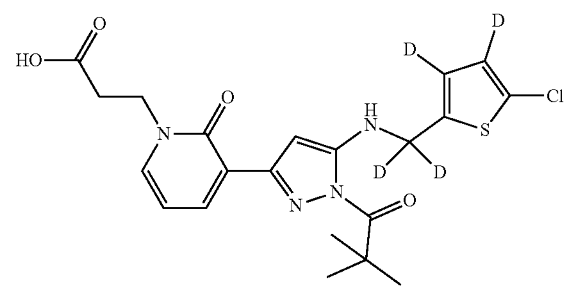 [SMILES: [2H]c1c(Cl)sc(C([2H])([2H])Nc2cc(-c3cccn(CCC(=O)O)c3=O)nn2C(=O)C(C)(C)C)c1[2H]] |
| 24 | 3-[3-(5-{[(5-chlorothiophen-2-yl)(2H2)methyl]amino}-1-(2,2-dimethylpropanoyl)-1H-pyrazol-3-yl)-2-oxo-1,2-dihydropyridin-1-yl]propanoic acid | 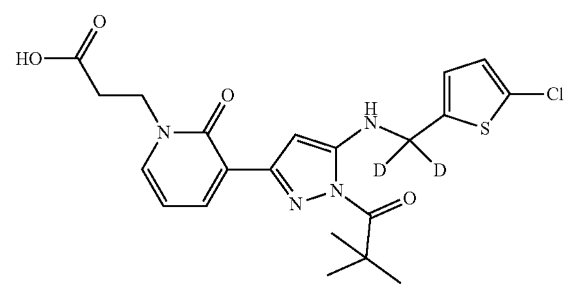 [SMILES: [2H]C([2H])(Nc1cc(-c2cccn(CCC(=O)O)c2=O)nn1C(=O)C(C)(C)C)c1ccc(Cl)s1] |

Compounds disclosed herein may also be present as mixtures with one or more additional compounds, and/or as mixtures including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography and the like. See e.g., Eliel, E. L. & Wilen S. H., 1993, STEREOCHEMISTRY IN ORGANIC COMPOUNDS; John Wiley & Sons, New York. In some embodiments, such mixtures include Compound 1, Compound 2, or both Compound 1 and Compound 2, wherein such mixtures can optionally further include isotopically-labeled and radio-labeled compounds, such as, for example, isotopically-labeled and radio-labeled versions of Compound 1, Compound 2, or both.

The compounds disclosed herein can also contain unnatural proportions of atomic isotopes at one or more of the atoms that constitute such compounds. For example, the compounds can be deuterated, and/or labeled with carbon-13 ($^{13}C$), and/or or radiolabeled with radioactive isotopes, such as, for example, tritium (3H) or carbon-14 ($^{14}C$); one skilled in the art will appreciate which isotopes can be present within the scope of the present invention. All isotopic variations of the compounds disclosed herein, whether radioactive or not, are encompassed within the contemplated scope. Exemplary deuterated compounds in accordance with the present invention include Compound Nos. 22, 23, and 24 in Table A; these compounds represent exemplary positions where compounds in accordance with the present invention can be deuterated, and one skilled in the art and with an understanding of chemistry principles will appreciate which compounds could be deuterated and at which positions, including but not limited to the positions shown in Compound Nos. 22, 23, and 24 in Table A.

In some embodiments, metabolites of the compounds disclosed herein are useful for the methods disclosed herein.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention can exist in multiple crystalline or amorphous forms. In general, all physical forms are equivalent for the compounds and methods contemplated herein and are intended to be within the scope disclosed herein.

III. Assays

Compounds described herein can be assayed by a variety of methods known in the art and described herein for a variety of chemical properties as well as various biological activities. For example, these parameters include thrombin inhibition, solubility and stability, and pharmacokinetic properties.

Human Thrombin Generation Assay

Results for the human thrombin generation assay (TGA; not to be confused with "thermogravimetric analysis" which is used elsewhere and carries the same acronym. One of skill in the art will appreciate which meaning is intended based on context of the surrounding technical information.) were generated as follows. In a 96-well plate, 4 µL of 100, 33.3, 11.1, 3.7, 1.23, 0.41, 0.137, and 0.046 µM solutions of the test compounds in DMSO were added to sequential wells filled with 68 µL of a "TGA Working Solution." See description of this solution as well as other relevant solutions below. The plate was incubated at room temperature for 10 minutes, whereupon 8 µL of warm "Substrate Solution" was added to each well, resulting in a 500 µM concentration of the substrate, Z-GGR-AMC (Z-Gly-Gly-Arg-7-amino-4-methylcoumarin·HCl), in each well. Fluorescence intensity data (Ex/Em 380/460 nm) collection began immediately using a Cytation™ or Synergy™ H1 96-well plate reader set to incubate the plate at 37° C. over the data collection time of 90 minutes following double-orbital shaking for a period of 4 seconds. Test compounds were measured parallel to blanks and controls, as well as to wells of the substrate in DMSO at various concentrations (2.50, 0.833, 0.278, 0.093 mM) in the buffers to generate a standard fluorescence curve. Data values were computed automatically, including the ETP $EC_{50}$ value of the AUC, which is the concentration of the compound that reduces endogenous thrombin potential AUC by 50%.

The various solutions were prepared as follows. A HEPES/NaCl Assay buffer was made by combining 7.5 mL of 5M NaCl, 1.19 g 4-(2-hydroxyethyl)piperazine-1-ethanesulfonic acid (HEPES) and 230 mL of water. An "Innovin Master Solution" was made by combining 20 µL of Siemens Dade Innovin recombinant tissue factor and thromboplastin with 50 µL of 0.5 mM phospholipid-TGT acquired from DiaPharma® in 450 µL of the above HEPES/NaCl Assay buffer. This solution was then vortexed for a few seconds. Next the "Substrate Master Solution" was made by adding 3.2 mL DMSO to 100 mg of Z-GGR-AMC (Z-Gly-Gly-Arg-7-amino-4-methylcoumarin·HCl) and vortexing in a polystyrene tube. This solution was stored at –20° C. A "TGA Working Solution" was prepared by adding 6.2 mL of human plasma, 50 µL of the Innovin Master Solution, and 80 µL of phospholipids to 2.6 mL of HEPES/NaCl Assay buffer.

A "Substrate Working Solution" was made immediately before addition to the assay plate by adding 200 µL of the above "Substrate Master Solution" to a pre-warmed (37° C.) mixture of 1.46 mL of HEPES/NaCl Assay buffer and 340 µL of 1M $CaCl_2$).

For additional description of this assay, please see Robert, S. et al. 'Is thrombin generation the new rapid, reliable and relevant pharmacological tool for the development of anticoagulant drugs?'2009, *Pharmacol Res* 59:160-6 as well as Hemker, H. C. et al. 'Calibrated automated thrombin generation measurement in clotting plasma.' 2003, *Pathophysiol Haemost Thromb* 33:4-15.

Mouse and Rat Plasma Stability

Results for the mouse (CD-1) and rat (SD) plasma stability were generated as follows. Alongside a positive control of propantheline bromide, 8 µL of a 1 mM solution of each test compound in DMSO was placed in two wells of a Nunc™ 96-well plate called the "dilution plate." To one well, 392 µL of HyClone™ water was added and mixed by a pipette. To the other well, 392 µL of mouse or rat plasma stabilized with sodium citrate purchased from Innovative Research was added and mixed by a pipette. The dilution plate was kept covered to reduce solvent evaporation and heated in an incubator at 37° C. At each of the time points enumerated below, the plate was removed from the incubator and 50 µL of the test compound/water or test compound/plasma solutions were transferred to a unique, corresponding well in a "quench plate" (96-well Costar® plate) that contains 150 µL of a quench solution that contains an internal standard (20 uM diclofenac in acetonitrile). The dilution plate was then returned to the incubator. This process was performed at 0, 5, 10, 20, 40, 80, and 160 minutes from the original mixing of the test compounds with the water or plasma in the dilution plate. After the quenching of the 160-minute time point, the quench plate was then centrifuged at 4° C. at 1000×g for 10 minutes. 100 µL of the supernatant of each well were then transferred to corresponding unique wells in a "read plate" (96-well Costar® plate) that were filled with 100 µL of HyClone™ water. The plate was then sealed and analyzed via UHPLC using a 10-µL sample injection through a Phenomenex® Kinetex column pre-equilibrated with the loading buffer (95:5 water:acetonitrile). The parameters were as follows. Mobile Phase A: water, 0.025% formic acid. Mobile Phase B: acetonitrile, 0.025% formic acid. Flow Rate: 0.5 mL/min. LC gradient: 0.0-0.5 min: hold 5% B; 0.5-2.5 min: 5%-95% B; 2.5-3.0 min: hold 95% B; 3.0-3.05 min: 95%-5% B; 3.0-4.0 min: hold 5% B. Absorbances were monitored at 254 nm and 280 nm, and compound concentrations were assumed to vary linearly with integrated peak areas obtained from the wavelength for which the compound shows a stronger absorbance. Half-life ($t_{1/2}$) times were computed by using a chi-square analysis to fit the peak areas to an exponential decay model for compound concentration as a function of time. If less than half of a half-life has elapsed by the last time point of 160 minutes, errors in the extracted half-life value are likely to be large. Therefore, in this document, half-life times calculated under these circumstances are reported as "≥300 min."

Mouse and Rat Liver Microsome Stability

Results for mouse (CD-1) and rat (SD) liver microsome stability were generated as follows. In a 96-well Nunc™ plate, 1.5 µL of a 200 µM solution of the test compound in DMSO were placed in a well. This plate, the "Reaction Plate," was then warmed to 37° C. in an oven. In a second 96-well Nunc™ plate, the "Quench Plate," six wells were filled with 180 µL of an internal standard quench solution composed of 100 nM diclofenac in acetonitrile. These six wells correspond to the six time points for data collection: 0, 0.5, 5, 15, 30, and 60 minutes. "Assay Buffer" was prepared by combining 6.96 g potassium phosphate, dibasic, 1.36 g potassium phosphate, monobasic, and 0.30 g of magnesium chloride hexahydrate, then diluting to a final concentration of 500 mL in water and adjusting to pH 7.4, as needed. Assay Buffer was warmed to 37° C., and 12 mL were added to a 10-mg vial of NADPH. Then 300 µL of a 20 mg/mL liver microsome suspension were added to yield a 0.5 mg/mL liver microsome suspension. 300 µL of this liver microsome suspension was then added to the test compound solution in the Reaction Plate and mixed thoroughly with a pipette tip. At each time point, 30 µL of this mixture was transferred to the corresponding well of the Quench Plate. In between time points, the Reaction Plate was kept sealed and warmed in an incubator at 37° C. When the last time point had been completed, the quench plate was centrifuged at 4° C. at 1000×g for 10 minutes. Afterwards, 50 µL of the supernatant of each well was transferred to unique, corresponding wells of a 96-well Costar® plate, the "Analysis Plate," filled with 150 µL of 50:50 acetonitrile:HyClone™ water. The Analysis Plate was then sealed with a pre-slit plate seal before analysis via an appropriate LCMS method with a 10 µL injection. The abstracted AUC data were then automatically plotted to calculate intrinsic clearance in µL/min/mg. This experiment was run alongside a positive and negative control. Due to the parameters of this procedure, one of skill in the art will appreciate that this assay has a lower measurable bound of 5 µL/min/mg; therefore, certain compounds have their clearances labeled as ≤5 µL/min/mg.

Mouse Pharmacokinetics

Mouse pharmacokinetic data were generated as follows. Compounds were administered intravenously (IV) as a single dose via tail vein or orally (PO) as a single dose via gastric gavage to male CD-1 mice with weights between 18 and 25 g. Nominal doses were 1 mg/kg and 5 mg/kg for IV and PO administration, respectively. The doses for IV were formulated by dissolving the test compound in a mixture (v/v/v) of 5% N,N-dimethylacetamide (DMA), 15% Kolliphor® (Solutol®) HS15, and 80% sterile water at a dose concentration of 0.25 mg/mL. Doses for PO were formulated by dissolving the test compound in a mixture (v/v) of 90% Kolliphor® (Solutol®) HS15 and 10% pure ethanol at a dose concentration of 0.25 mg/mL.

Animals were housed in standard holding cages with food and water available ad libitum except for those used for PO dosing, which were fasted overnight prior to dosing. Prior to dosing and at each time point following dosing (5 min (IV only), 15 min, 30 min, 60 min, 120 min, 4 h, 8 h, 12 h, and 24 h), two animals were sacrificed and blood samples were taken in triplicate via cardiac puncture. Plasma was obtained by centrifuge and stored frozen until analyzed by LC-MS/MS using an AB Sciex™ QTrap® 5500 coupled to a Shimadzu Nexera X2 fitted with a Luna® Omega 1.6 µm Polar C18 100 Å, 50×2.1 mm, acquired from Phenomenex®. Samples were compared against a standard curve of the test compound at concentrations ranging from 10,000 to 0.3 ng/mL.

Pharmacokinetic parameters are calculated from mean concentration values using a non-compartmental analysis as described below and as apparent to those of ordinary skill in the art. Concentration at time zero ($C_0$) for the IV was established by the extrapolation of log-linear regression using equal weighting on the first three sample time points. Area under the curve (AUC) values were calculated using linear trapezoidal integration.

Rat Pharmacokinetics

Rat pharmacokinetic data were generated as follows. Compounds were administered intravenously (IV) via tail vein or orally (PO) via gastric gavage to Sprague-Dawley rats fitted with surgically implanted jugular vein catheters (JVC) with nominal weights between 250 and 275 g. Nominal doses were 1 mg/kg and 5 mg/kg for IV and PO, respectively. The doses for IV administration were formulated by dissolving the test compound in a mixture (v/v/v) of 5% N,N-dimethylacetamide (DMA), 15% Kolliphor® (Solutol®) HS15, and 80% sterile water at a dose concentration of 0.25 mg/mL. The doses for PO administration were formulated either as Option A or Option B. Option A was formulated by dissolving the test compound in a mixture (v/v) of 90% Kolliphor® (Solutol®) HS15 and 10% pure ethanol at a dose concentration of 0.25 mg/mL. Option B was formulated by dissolving the test compound in a mixture (v/v) of 20% Labrasol® and 80% Phosphate buffer at pH 6.8.

Animals were housed in standard holding cages with food and water available ad libitum except for animals used for PO dosing which were fasted overnight prior to dosing. One to three rats were used for each experiment. Samples were collected manually via its JVC just before the dosing, as well as at the time points of 5 min, 15 min, 30 min, 60 min, 120 min, 4 h, 8 h, 12 h, and 24 h. Alternatively, samples were collected automatically by transferring the animal to a BASi Culex® automated blood-sampling system for the duration of the experiment. Plasma was obtained by centrifuge and stored frozen until analyzed by LC-MS/MS using an AB Sciex™ QTrap® 5500 coupled to a Shimadzu Nexera X2 fitted with a Luna® Omega 1.6 µm Polar C18 100 Å, 50×2.1 mm, acquired from Phenomenex®. Samples were compared against a standard curve of the test compound at concentrations ranging from 10,000 to 0.3 ng/mL.

Pharmacokinetic parameters were calculated from mean concentration values using a non-compartmental analysis as described below and as apparent to those of ordinary skill in the art. Concentration at time zero ($C_0$) for the IV was established by the extrapolation of log linear regression using equal weighting on the first three sample time points. Area under the curve (AUC) values were calculated using linear trapezoidal integration.

Inhibition of Platelet Activation in CD-1 Mouse Plasma

Assays for inhibition of platelet activation in mouse plasma were performed by the following procedure. Test compounds and positive controls were first diluted in a three-fold series in DMSO to generate a range of concentrations for each from 1500 to 0.08 µM. 2 µL of each sample solution was then placed in corresponding wells of a 96-well plate (the "assay plate") containing 88 µL of a platelet-rich plasma (PRP) mix described below. 10 µL of a 10 nM solution of mouse thrombin in assay buffer (described below) was then added to each well of the assay plate. The plate was then shaken on a Lab-Line Instruments Inc. titer plate shaker for 2 minutes at 300 RPM. 10 uL of Chrono-Lume® solution was then added to each well. The plate was again shaken for 3 minutes at 300 RPM. Luminescence data were recorded from a plate reader. Each sample was measured in duplicate and against blanks with and without mouse thrombin to record background and maximum signal measurements. The $IC_{50}$ data were automatically calculated from the measured luminescence counts by means appreciated by one of skill in the art.

The various solutions involved in this procedure are described as follows. Assay buffer was made by combining 7.5 mL of 5 M NaCl with 1.19 g of HEPES powder, 0.5 mL of 1 M MgCl$_2$, 1.5 mL of 1 M KCl and 235 mL of water in a 500 mL flask. The solution's pH was adjusted to 7.4 using 10 N NaOH, and then brought up to a final volume of 250 mL using water. A 20 mM solution of H-Gly-Pro-Arg-Pro-OH (GPRP) in this assay buffer was made from commercially obtained powder. The PRP Mix was made by first centrifuging down 600 µL of whole CD-1 mouse blood in 1.8 mL sodium citrate vacutainers at 100×g for 10 minutes at room temperature in an Eppendorf 5810 R centrifuge. The plasma layer was then extracted along with as much as possible of the buffy coat into storage vials. Extractions from multiple animals were often pooled together. To make the final mix, 2.3 mL of these plasma extractions was combined with 7.2 mL of the above assay buffer and 0.5 mL of the 20 mM GPRP solution. In this final PRP mix, the platelet count was about 200×10$^6$ mL$^{-1}$. The mouse thrombin solution was made by mixing mouse thrombin acquired from Haematological Technologies, Inc. in the above assay buffer to generate a 100 nM solution.

Biological Activities

The below presentation of biological data is meant to illustrate various aspects of the embodiments and is not intended to limit the disclosure.

Table B below shows the ETP EC$_{50}$ values for selected compounds in the Human Thrombin Generation Assay; "ND" indicates compounds for which data was not available at the time of filing.

TABLE B

| Compound No. | ETP EC$_{50}$ (µM) |
| --- | --- |
| 1 | 0.93-1.7 |
| 2 | >100 |
| 3 | >100 |
| 4 | 2.8-6.2 |
| 5 | 1.4 |
| 6 | 5.4 |
| 7 | 0.85-0.97 |
| 8 | 0.99 |
| 9 | 0.43 |
| 10 | 1.7-10 |
| 11 | 0.96 |
| 12 | 1.4-2.1 |
| 13 | ND |
| 14 | ND |
| 15 | 2.9 |
| 16 | 1.9 |
| 17 | 1.2 |
| 18 | 1.3 |
| 19 | ND |
| 20 | 2.4 |
| 21 | 4.8 |
| 22 | 1.9 |
| 23 | ND |
| 24 | 2.4 |

Table C below shows the mouse and rat plasma stabilities and liver microsome clearances for selected compounds.

TABLE C

| Compound No. | Mouse Plasma Stability t$_{1/2}$ (min) | Mouse Liver Microsomal Stability CL$_{int}$ (µL/min/mg) | Rat Plasma Stability t$_{1/2}$ (min) | Rat Liver Microsomal Stability CL$_{int}$ (µL/min/mg) |
| --- | --- | --- | --- | --- |
| 1 | 180-≥300 | ≤5-11 | 68-110 | ≤5 |
| 2 | ≥300 | ≤5 | ≥300 | ≤5 |
| 3 | ≥300 | ≤5 | ≥300 | ≤5 |
| 4 | ≥300 | ≤5 | 180 | ≤5 |
| 5 | 230 | 29 | 68 | 10 |
| 6 | 7 | 9 | — | — |
| 7 | ≥300 | 290 | — | — |
| 8 | 160 | 100 | 68 | — |
| 9 | 160 | 11 | 68 | ≤5 |
| 10 | 70 | 4 | — | — |
| 11 | ≥300 | 31 | ≥300 | 14 |
| 12 | 220 | ≤5 | 180 | — |

Table D below shows various pharmacokinetic data of selected compounds in CD-1 mice.

TABLE D

| Compound No. | IV C$_0$ (ng/mL) | IV AUC (h · ng/mL) | PO C$_{max}$ (ng/mL) | PO AUC (h · ng/mL) |
| --- | --- | --- | --- | --- |
| 1 | 6800 | 8200 | 3600 | 31000 |
| 2 | 6300 | 850 | 700 | 1300 |
| 3 | 7200 | 2200 | — | — |
| 4 | 9500 | 6200 | 1500 | 15000 |
| 8 | 1700 | 530 | — | — |
| 11 | 7400 | 3900 | — | — |
| 12 | 4200 | 1000 | — | — |

Table E below shows various pharmacokinetic data of selected compounds in SD rats.

TABLE E

| Compound No. | Formulation | IV C$_0$ (ng/mL) | IV AUC (h · ng/mL) | PO C$_{max}$ (ng/mL) | PO AUC (h · ng/mL) |
| --- | --- | --- | --- | --- | --- |
| 1 | A | 6500 | 3000 | 240 | 2200 |
| 2 | B | 5600 | 760 | 150 | 140 |
| 4 | A | 12000 | 2300 | 260 | 2300 |
| 5 | B | 5400 | 3300 | 930 | 2100 |
| 8 | B | — | — | 230 | 120 |
| 9 | B | 94 | 180 | 5.8 | 73 |
| 11 | B | 6100 | 3200 | 1200 | 2100 |
| 12 | A | 4600 | 930 | 19 | 28 |

Table F below shows the EC$_{50}$ of selected compounds towards inhibited platelet activation in CD-1 mice.

TABLE F

| Compound No. | EC$_{50}$ (µM) |
| --- | --- |
| 1 | 15 |
| 4 | 15 |
| 9 | 0.032 |

IV. Methods of Treating and Preventing Disease

Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

Generally, the terms "treating," "treatment" and the like are used herein to mean affecting a subject, tissue or cell to obtain a desired pharmacologic and/or physiologic effect.

The effect can be prophylactic in terms of completely or partially preventing a disease or disorder or sign or symptom thereof, and/or can be therapeutic in terms of a partial or complete cure for a disorder and/or adverse effect attributable to it, e.g. pulmonary embolism following a medical procedure. "Treating" as used herein covers any treatment of, or prevention of a disease or disorder in a vertebrate, a mammal, particularly a human, and includes: (a) preventing the disease or disorder from occurring in a subject that can be predisposed to the disease or disorder but has not yet been diagnosed as having it; (b) inhibiting the disease or disorder, i.e., arresting its development; or (c) relieving or ameliorating the disease or disorder, i.e. cause regression of the disease or disorder.

It has been discovered that compounds described herein, e.g., 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid as well as compounds depicted in Table A exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-arterial- and cardiogenic thromboembolisms; the prevention of other states such as disseminated intravascular coagulation, or other conditions that involve the presence or the potential formation of a blood clot thrombus. Other indications for methods described herein below.

Known thrombin inhibitors have been reported to be useful in the treatment and prevention of acute coronary syndrome (ACS) (Clemens, A. et al. WIPO Patent Application WO/2008/009638). ACS is a group of symptoms that are caused by myocardial ischemia. The drug could be used as a prophylaxis for myocardial infarction, or a certain time after the event (e.g. after myocardial infarction, post-MI; i.e. chronic therapy, secondary prevention). Without further wishing to be bound by any theory, it is reasonable to believe that thrombin inhibition in general can be useful in treating and preventing acute coronary syndrome.

Non-valvular atrial fibrillation is a sustained cardiac disturbance often associated with heart disease. Known thrombin inhibitors like ximelagatran have been reported to be useful for stroke prevention in patients with non-valvular atrial fibrillation (Diener H.-C. *Cerebrovasc Dis* 2006; 21:279-293).

The selective thrombin inhibitor ximelagatran was studied in two phase III clinical trials ((SPORTIF III and SPORTIF V), which compared ximelagatran to warfarin for the prevention of cardioembolic events in patients with non-valvular atrial fibrillation. The investigators for the SPORTIF III clinical trial found that ximelagatran, administered in a fixed dose without coagulation monitoring, protects high-risk patients with atrial fibrillation against thromboembolism at least as effectively as well-controlled warfarin, and is associated with less bleeding. When the results of SPORTIF III and V were combined, ximelagatran was associated with a 16% relative risk reduction in the composite outcome measure of all strokes (ischemic or hemorrhagic), systemic embolic events, major bleeding, and death. (Olsson, S. B., 2003, *Lancet,* 362 (9397): 1691-1698; Hirsh, J., 2005 et al. *Blood,* 105 (2): 453-463; Clemens, A. et al. WIPO Patent Application WO/2008/009638). Without further wishing to be bound by any theory, it is reasonable to believe that thrombin inhibition in general can be useful in preventing stroke in individuals with atrial fibrillation.

A Transient Ischemic Attack (TIA) is an acute episode of temporary neurologic dysfunction that typically lasts less than an hour; results from focal cerebral, spinal cord, or retinal ischemia; and is not associated with acute tissue infarction. In people who have a TIA, the incidence of subsequent stroke is as high as 11% over the next 7 days and 24-29% over the following 5 years. In view of the high short-term risk of stroke after TIA, many physicians believe antithrombotic therapy should be initiated as soon as intracranial hemorrhage has been ruled out. Stroke prevention medication typically recommended for cardioembolic TIA is as follows: For patients with atrial fibrillation after TIA, long-term anticoagulation with warfarin (aspirin 325 mg/day for those unable to take oral anticoagulants); In acute myocardial infarction (MI) with left ventricular thrombus, oral anticoagulation with warfarin; concurrent aspirin up to 162 mg/day for ischemic coronary artery disease [CAD]); In dilated cardiomyopathy, oral anticoagulation with warfarin or antiplatelet therapy; In rheumatic mitral valve disease, oral anticoagulation with warfarin. For patients with TIA and ischemic stroke of cardiac origin due to atrial fibrillation, vitamin K antagonists (VKAs) are highly effective in preventing recurrent ischemic stroke but have important limitations and are thus underused. Antiplatelet therapy is much less effective than VKAs. The direct thrombin inhibitor, dabigatran etexilate, has shown efficacy over warfarin in a trial. Other new anticoagulants, including the oral factor Xa inhibitors, rivaroxaban, apixaban, and edoxaban, the parenteral factor Xa inhibitor, idrabiotaparinux, and the novel VKA, tecarfarin, were being assessed in 2010. (Hankey, G. J.; Eikelboom, J. W., 2010, 'Antithrombotic Drugs for Patients with Ischaemic Stroke and Transient Ischaemic Attack to Prevent Recurrent Major Vascular Events.' *The Lancet Neurology,* 9 (3): 273-284.)

Known thrombin inhibitors have been reported to be useful for the treatment of venous thromboembolism due to formation of a thrombus within a vein (venous thrombosis) associated with acquired (prolonged bedrest, surgery, injury, malignancy, pregnancy and postpartum states) or inherited (deficiency of natural coagulation inhibitors) risk factors (Marsic, L. P. et al. WIPO Patent Application WO/2003/048155). Without further wishing to be bound by any theory, it is reasonable to believe that thrombin inhibition in general can be useful for the treatment of venous thromboembolism due to formation of a thrombus within a vein associated with acquired or inherited risk factors and/or embolism of peripheral veins caused by a detached thrombus. An example of an acquired risk factor would be a previous venous thromboembolism.

Known thrombin inhibitors have been reported to be useful for the treatment of cardiogenic thromboembolism due to formation of a thrombus in the heart associated with cardiac arrhythmia, heart valve defect, prosthetic heart valves or heart disease, embolism of peripheral arteries caused by a detached thrombus, most commonly in the brain (ischemic stroke). See Marsic, L. P. et al. WIPO Patent Application WO/2003/048155. Without further wishing to be bound by any theory, it is reasonable to believe that thrombin inhibition in general can be useful for the treatment of cardiogenic thromboembolism.

Known thrombin inhibitors have been reported to be useful for the treatment of arterial thrombosis due to underlying atherosclerotic processes in the arteries which obstructs or occludes an artery and causes myocardial ischemia (angina pectoris, acute coronary syndrome) or myocardial infarction, obstructs or occludes a peripheral artery (ischemic peripheral artery disease) and obstructs or occludes the artery after the procedure on the blood vessel (reocclusion or restenosis after transluminal coronary angioplasty, reocclusion or restenosis after percutaneous transluminal angioplasty of peripheral arteries). See Marsic, L. P. et al. WIPO Patent Application WO/2003/048155. Without further wishing to be bound by any theory, it is reasonable to believe that thrombin inhibition in general can be useful for the treatment of arterial thrombosis.

Known thrombin inhibitors have been reported to be useful in the prevention of recurrent cardiac events after myocardial infarction. The selective thrombin inhibitor ximelagatran was studied in a phase II clinical trial entitled ESTEEM, measuring the efficacy and safety of the oral direct thrombin inhibitor ximelagatran in patients with recent myocardial damage. The result of the ESTEEM trial supports the notion that long-term treatment with an oral direct thrombin inhibitor reduces arterial thrombotic events. Oral ximelagatran in combination with acetylsalicylic acid was more effective than acetylsalicylic acid alone in reducing the frequency of major cardiovascular events during 6 months of treatment in patients with a recent myocardial infarction. (Hirsh, J., 2005, et al. *Blood,* 105 (2): 453-463.). Without further wishing to be bound by any theory, it is reasonable to believe that thrombin inhibition in general can be useful in preventing recurrent cardiac events after myocardial infarction.

Known thrombin inhibitors have been reported to be useful in post-operative prophylaxis of deep vein thrombosis. The selective thrombin inhibitor ximelagatran was found to be efficacious for the prevention of venous thromboembolism after following a medical procedure like total hip or knee replacement (Francis, C. W. et al., 2002, *Ann Intern Med,* 137:648-55; Heit, J. A., 2001, et al. *Arch Intern Med,* 161: 2215-21; Eriksson B I et al., 2003, *Thromb Haemost,* 89: 288-96). Without further wishing to be bound by any theory, it is reasonable to believe that thrombin inhibition in general can be useful in post-operative prophylaxis of deep vein thrombosis.

Known thrombin inhibitors like dabigatran have been reported to be useful in long-term treatment of pulmonary embolism. (Robertson L, Kesteven P, McCaslin J E. *Cochrane Database Syst Rev.* 2015 Dec. 4; 12). Without further wishing to be bound by any theory, it is reasonable to believe that thrombin inhibition in general can be useful in treating pulmonary embolism.

Known thrombin inhibitors have been reported to be useful for the treatment of pulmonary-arterial hypertension. Dabigatran, a selective thrombin inhibitor, has been published as a useful drug for the treatment of pulmonary-arterial hypertension (PAH). Furthermore, dabigatran had found use as a treatment of: (i); pulmonary hypertension caused by left heart disorders, (ii); pulmonary hypertension associated with lung diseases such as pulmonary fibroses, particularly idiopathic pulmonary fibrosis, and/or hypoxia, (iii); pulmonary hypertension caused by chronic thromboembolic diseases. (Feuring, M. WIPO Patent Application WO/2010/020600). Without further wishing to be bound by any theory, it is reasonable to believe that thrombin inhibition in general can be useful for the treatment of pulmonary-arterial hypertension.

Known thrombin inhibitors have been reported to be useful for the treatment of pulmonary-arterial hypertension caused by left heart disorders (Feuring, M. WIPO Patent Application WO/2010/020600). Without further wishing to be bound by any theory, it is reasonable to believe that thrombin inhibition in general can be useful for the treatment of pulmonary-arterial hypertension caused by left heart disorders.

Known thrombin inhibitors have been reported to be useful for the treatment of pulmonary-arterial hypertension associated with lung diseases such as pulmonary fibroses, particularly idiopathic pulmonary fibrosis, and/or hypoxia (Feuring, M. WIPO Patent Application WO/2010/020600). Without further wishing to be bound by any theory, it is reasonable to believe that thrombin inhibition in general can be useful for the treatment of pulmonary-arterial hypertension associated with lung diseases.

Known thrombin inhibitors have been reported to be useful for the treatment of pulmonary hypertension caused by chronic thromboembolic diseases (Feuring, M. WIPO Patent Application WO/2010/020600). Without further wishing to be bound by any theory, it is reasonable to believe that thrombin inhibition in general can be useful for the treatment of pulmonary hypertension caused by chronic thromboembolic diseases.

Known thrombin inhibitors have been reported to be useful for the treatment of disseminated intravascular coagulation in a number of states (e.g., in complications in pregnancy, in metastasing malignant diseases, after extensive injuries, in bacterial sepsis) when thrombogenic activation causes dysfunctional coagulation with widespread formation of thrombii within the vascular system. See Marsic, L. P. et al. WIPO Patent Application WO/2003/048155. Without further wishing to be bound by any theory, it is reasonable to believe that thrombin inhibition in general can be useful for the treatment of disseminated intravascular coagulation.

Known thrombin inhibitors have been reported to be useful for the prevention of coagulation in patients undergoing percutaneous coronary intervention. Percutaneous coronary intervention (PCI) requires aggressive anticoagulation therapy and was historically achieved with unfractionated heparin. However, in many patients, heparin is contraindicated, especially in patients with heparin-induced thrombocytopenia (HIT). In such instances, the endovascular disruption and the hypercoagulable state that characterized HIT means patients are put at risk of thrombosis during PCI. (Lewis, B. E. et al., 2002, *Catheterization and cardiovascular interventions,* 57 (2): 177-184; Kokolis, S et al., 2004, *Progress in cardiovascular diseases,* 46 (6): 506-523.) Dabigatran, which had already been claimed as a thrombin inhibitor and a useful anticoagulant in the clinical setting, was also published as a secondary medication in percutaneous interventional cardiac catherization. (Reilly et al. WIPO Patent Application WO/2010/020602). Without further wishing to be bound by any theory, it is reasonable to believe that thrombin inhibition in general can be useful in preventing coagulation in patients undergoing percutaneous coronary intervention.

Known thrombin inhibitors have been reported to be useful as an adjunct therapy in conjunction with thrombolytic therapy in recent myocardial infarction, in combination with aspirin in patients with unstable angina pectoris designed to undergo percutaneous transluminal angioplasty and in the treatment of patients with thrombosis and with heparin-induced thrombocytopenia (Marsic, L. P. et al. WIPO Patent Application WO/2003/048155). Without further wishing to be bound by any theory, it is reasonable to believe that thrombin inhibition in general can be useful as an adjunct therapy with other antithrombotic therapies.

It has long been recognized that cancer progression is accompanied by venous thrombosis, but it has not been understood how each disease is related. From several clinical trials studying the treatment of VTE, meta-analyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. Petal., *J Clin Oncol* 2005, 23:2130-2135; Kakkar, A. K., et al., 2004, *J Clin Oncol*, 22:1944-1948; Altinbas, M., et al., 2004, *J Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir*, Suppl 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver micrometastases by 50-60%. These investigators concluded that dabigatran etexilate can be beneficial in not only preventing thrombotic events in cancer patients, but also as adjunct therapy to treat malignant tumors.

Additional studies have investigated the applicability of anticoagulants towards treating patients with coronary artery disease and/or peripheral artery disease. The COMPASS trial saw improved cardiovascular outcomes to patients treated with rivaroxaban in combination with antiplatelet treatment. See, e.g., Eikelboom, J. W., et al. 2017, *N Engl J Med*, 377:1319-30. Furthermore, the COMMANDER trial has investigated the utility of rivaroxaban towards improved cardiovascular outcomes in patients with coronary artery disease, including those who are developing heart failure, and in particular, heart failure with reduced ejection fraction (IF-rEF). See, e.g., Zannad, F., et al., 2015 *European Journal of Heart Failure*, 17:735-42. Therefore, it is suggested that an anticoagulant can be useful for adjunct therapy in subjects with at least one of coronary artery disease and heart failure and wherein the adjunct therapy further includes antiplatelet therapy.

The European Society of Cardiology recommends the use of an anticoagulant in combination with antiplatelet therapy for patients with valvular or non-valvular atrial fibrillation and at least one prior acute coronary syndrome event. See, e.g. Kirchhof, P., et al., 2016, *European Heart Journal*, 37:2893-2962. Therefore, it is suggested that an anticoagulant can be useful for adjunct therapy in subjects with atrial fibrillation and at least one of coronary artery disease and heart failure and wherein the adjunct therapy further includes antiplatelet therapy. The European Cardiology Society also recommends the use of an anticoagulant in combination with antiplatelet therapy for subjects with valvular or non-valvular atrial fibrillation undergoing an elective percutaneous coronary intervention (PCI) with a stent. See, e.g., Kirchhof, P., et al., 2016, *European Heart Journal*, 37:2893-2962. Therefore, it is suggested that an anticoagulant can be useful for adjunct therapy in subjects having valvular or non-valvular atrial fibrillation undergoing a percutaneous coronary intervention with a stent and wherein the adjunct therapy further includes antiplatelet therapy.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., 2010, *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration. Similar observations were made in other studies using the LMWHs nadroparin, tinzaparin, enoxaparin, and dalteparin sodium. See e.g., Duplantier, J. G., et al., 2004, *Gut*, 53:1682-1687; Abdel-Salam, O. M., et al., 2005, *Pharmacol Res*, 51:59-67; Assy, N., et al., 2007, *Dig Dis Sci*, 52:1187-1193; Abe, W., et al., 2007, *J Hepatol*, 46:286-294. Thus, a thrombin inhibitor as an anticoagulant can be useful in the treatment of fibrinolytic diseases.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant*, 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.*, 181:A6780; Bogatkevich, G. S., et al., 2009, *Arthritis Rheum*, 60:3455-3464.

The above experimental evidence points to a close relationship between thrombin and fibrosis and suggests novel therapeutic opportunities for fibrosis using thrombin inhibitors. See e.g., Calvaruso, V., et al., 2008, *Gut*, 57:1722-1727; Chambers, R. C., 2008, *Br J Pharmacol*, 153 Suppl 1:S367-378; Chambers, R. C. & Laurent, G. J., 2002, *Biochem Soc Trans*, 30:194-200; Howell, D. C., et al., 2001, *Am J Pathol*, 159:1383-1395.

Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res,* 668:160-170; Yin, X., et al., 2010, *Am J Pathol,* 176:1600-1606; Akiyama, H., et al., 1992, *Neurosci Lett,* 146:152-154.

Investigators found that hirudin treatment in an animal model of Multiple Sclerosis (MS) showed a dramatic improvement in disease severity. See e.g., Han, M. H., et al., 2008, *Nature,* 451:1076-1081. Similar results were obtained following treatment with heparin (a DTI) and dermatan sulfate, another coagulation inhibitor. See e.g., Chelmicka-Szorc, E. & Arnason, B. G., 1972, *Arch Neurol,* 27:153-158; Inaba, Y., et al., 1999, *Cell Immunol,* 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca,* 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief. See e.g., Garcia, P. S., et al., 2010, *Thromb Haemost,* 103:1145-1151; Narita, M., et al., 2005, *J Neurosci,* 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, Id. Known thrombin inhibitors have been reported to be useful for the treatment of inflammation (Kirk, I. WIPO Patent Application WO/2000/041716), type I diabetes mellitus (Korsgren, O.; Nillson, B. WIPO Patent Application WO/2003/061682), cancer (Kakkar, A. K. et al., 2004, *J Clin Oncol,* 2, (10): 1944-8; Hua, Y. et al., 2005, *Acta Neurochir Suppl,* 95: 403-6; Nieman, M. T. et al., 2008, *J Thromb Haemost,* 6: 837-845; Van Ryn, J.; Clemens, A. WIPO Patent Application WO/2010/020601), fibrosis (Duplantier, J. G. et al., 2004, *Gut,* 53:1682-1687; Seijo, S. et al., 2007, *J Hepatol,* 46:286-294; Assy, N. et al., 2007, *Dig Dis Sci,* 52:1187-1193; Bogatkevich, G. S. et al., 2009, *Arthritis Rheum,* 60:3455-3464), and pain (Garcia, P. S. et al., 2010, *Thromb Haemost,* 103:1145-1151; Narita, M. et al., 2005, *J Neurosci,* 25:10000-10009). Metaanalyses of clinical trials that studied the use of anticoagulants in oncology patients showed that low molecular weight heparins (LMWHs), selective thrombin inhibitors, improve overall survival in subgroups of cancer patients. This finding was substantiated in later clinical trials, in particular the FAMOUS clinical trials, that measured specifically the survival of cancer patients. Without further wishing to be bound by any theory, it is reasonable to believe that thrombin inhibition in general can be useful for the treatment of inflammation, diabetes mellitus, cancer, fibrosis, or pain.

V. Pharmaceutical Compositions

In another aspect, there is provided a pharmaceutical composition comprising a compound disclosed herein and a pharmaceutically acceptable excipient. The compound is a compound of Structure I as disclosed herein, or a compound as set forth as Compound 1 or Compound 2 herein, or pharmaceutically acceptable salt or solvate thereof.

The term "pharmaceutically acceptable salts" is meant to include salts of the active compounds that are prepared with relatively nontoxic acids or bases, depending on the particular substituents found on the compounds described herein. This treatment of the active compounds with relatively nontoxic acids or bases generates an ionic form of the active compound and a counterion.

When compounds disclosed herein contain relatively acidic functionalities such as such as —$NHSO_3H$, —COOH and —$P(O)(OH)_2$, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt.

In certain embodiments, the compound is compound I and the counterion is selected from the group consisting of sodium, potassium, calcium, L-arginine, L-lysine, meglumine, and tris(hydroxymethyl)aminomethane.

Certain specific compounds disclosed herein contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition, some of the compounds disclosed herein can form solvates with water or common organic solvents. Such solvates are encompassed within the scope of the methods contemplated herein.

Furthermore, some embodiments include cocrystals including compounds disclosed herein. A cocrystal can be understood as any single material in crystalline form that comprises two or more distinct chemical matters, known as coformers, in a defined stoichiometric ratio that cannot otherwise be classified as a salt or solvate. One skilled in the art would appreciate which coformers could be used in accordance with the present invention to form cocrystals with the presently claimed compounds. For example, the Food and Drug Administration (FDA) Select Committee on GRAS Substances (SCOGS) maintains a number of common coformers in their database of Generally Regarded As Safe (GRAS) substances, and which can be used in accordance with the present invention to form cocrystals with the presently claimed compounds. As of July 2019, the SCOGS list included the GRAS substances listed in Table G below. One skilled in the art will appreciate that the FDA may update, revise, or rename this list over time and that additional compounds may be generally regarded as safe, and that such compounds can be used in accordance with the present invention as well. Coformers can include one or more counterions, such as, for example, sodium, potassium, calcium, L-arginine, L-lysine, meglumine, and tris(hydroxymethyl)aminomethane, and the like. Accordingly, the invention encompasses cocrystals with compounds from an FDA-maintained list of GRAS substances, or with the compounds listed in Table G, or with other compounds which are generally regarded as safe, and/or can include one or more counterions, such as, for example, sodium, potassium, calcium, L-arginine, L-lysine, meglumine, and tris(hydroxymethyl)aminomethane, and the like.

TABLE G

GRAS Substance

Acetic acid
Acetylated Distarch Adipate
Acetylated Distarch Glycerol
Acetylated Distarch Phosphate
Acetylated Distarch Oxypropanol
Acid Modified Starch
Aconitic Acid
Adipic acid
Agar-agar
Allyl isothiocyanate
Aluminum ammonium sulfate
Aluminum calcium silicate
Aluminum hydroxide
Aluminum oleate (packaging)
Aluminum palmitate (packaging)
Aluminum potassium sulfate
Aluminum sodium sulfate
Aluminum sulfate
Ammonium alginate
Ammonium bicarbonate
Ammonium carbonate
Ammonium chloride
Ammonium citrate
Ammonium hydroxide
Ammonium phosphate dibasic (Report 32)
Ammonium phosphate dibasic (Report 34)
Ammonium phosphate monobasic (Report 32)
Ammonium phosphate monobasic (Report 34)
Ammonium sulfate
Arrowroot Starch
L-Ascorbic acid
Ascorbyl palmitate (palmitoyl L-ascorbic)
Beeswax (yellow or white)
Bentonite
Benzoic Acid
Biotin
Bleached Starch
Brown algae
Butylated Hydroxyanisole (BHA)
Butylated Hydroxytoluene (BHT)
Caffeine
Calcium acetate
Calcium alginate
Calcium carbonate
Calcium caseinate
Calcium chloride
Calcium citrate
Calcium gluconate
Calcium glycerophosphate
Calcium glycerophosphate (packaging)
Calcium hexametaphosphate
Calcium hydroxide
Calcium hypophosphite
Calcium iodate
Calcium L-ascorbate
Calcium Lactate
L(+)-calcium lactate
Calcium oxide
D- or DL- Calcium pantothenate
Calcium phosphate dibasic
Calcium phosphate monobasic
Calcium phosphate tribasic
Calcium phytate
Calcium propionate
Calcium pyrophosphate
Calcium silicate
Calcium sorbate TABLE G-continued GRAS Substance Calcium stearate
Caprylic Acid
Caramel
Carbon dioxide
Carbonyl Iron
Carbonyl Iron (packaging)
Carboxymethyl cellulose (packaging)
Carnauba wax
Carob Bean Gum
Carotene (beta-carotene)
Carrageenan
Casein
Enzymatically hydrolyzed casein
Cellulose
Cellulose acetate(packaging)
Cellulose, microcrystalline
Cholic acid
Choline Bitartrate
Choline Chloride
Citric acid
Clay (kaolin) (packaging)
Clove Bud Extract
Clove Bud Oil
Clove Bud Oleoresin
Clove Leaf Oil
Clove Stem Oil
Coconut oil (packaging)
Copper (cupric) gluconate
Copper (cupric) sulfate
Corn silk
Corn Sugar (Dextrose)
Corn Syrup
Cornstarch
Cuprous iodide
Desoxycholic acid
Dextran
Dextrins
Corn dextrins (packaging)
Diacetyl
Diatomaceous earth (filter aid)
Dietary Iron
Dilauryl thiodipropionate
Distarch Glycerol
Distarch Oxypropanol
Distarch Phosphate
Electrolytic Iron
Electrolytic Iron (packaging)
Erythorbic acid (D-isoascorbic acid)
Ethyl acrylate, monomeric (packaging)
Ethyl acrylate, polymeric (packaging)
Ethyl cellulose (packaging)
Ethyl formate
Ferric ammonium citrate
Ferric chloride (packaging)
Ferric citrate
Ferric oxide
Ferric oxide (packaging)
Ferric phosphate
Ferric pyrophosphate
Ferric sodium pyrophosphate
Ferric sulfate (packaging)
Ferrous ascorbate
Ferrous carbonate
Ferrous citrate
Ferrous fumarate
Ferrous gluconate
Ferrous lactate
Ferrous sulfate
Ferrous sulfate (packaging)
Fish oil, hydrogenated (packaging)
Formic acid (packaging)
Garlic and Oil of Garlic
Gelatin
L-Glutamic acid
L-Glutamic acid hydrochloride
Glycerin and Glycerides
Glycocholic acid
Glycyrrhiza TABLE G-continued GRAS Substance Ammoniated Glycyrrhizin
Guar Gum
Gum Arabic
Gum Ghatti
Gum guaiac
Gum Tragacanth
Helium gas
High Amylose Cornstarch
Hydrochloric acid
Hydrogen peroxide
Hydrogenated soybean oil
Hydrogenated tallow (packaging)
p-Hydroxybenzyl isothiocyanate
Hydroxypropyl Distarch Glycerol
Hydroxypropyl Distarch Phosphate
Hydroxypropyl Starch
Hydroxypropyl Starch, oxidized
Hydroxypropylmethyl cellulose
Indian Dill Seed
Inositol
Invert Sugar
Iron - Report on Bioavailability and Utilization of Iron
Iron - Report on Clinical Research Protocols to Elucidate The Possible Hazards of Increased Iron Enrichment of Cereal Products
Iron caprylate (packaging)
Iron linoleate (packaging)
Iron naphthenate
Iron oxides (packaging)
Iron peptonate
Iron polyvinylpyrrolidone
Iron tallate (packaging)
Iron, elemental (packaging)
Isopropyl citrate
Japan wax (packaging)
D(−)-Lactic acid
Lactic acid
L(+)-lactic acid
Lard (packaging)
Lard oil (packaging)
Lecithin
Lecithin, hydrogen peroxide bleached
Licorice
Linoleic acid
Magnesium carbonate
Magnesium chloride
Magnesium gluconate
Magnesium glycerophosphate (packaging)
Magnesium hydroxide
Magnesium oxide
Magnesium phosphate, dibasic
Magnesium phosphate, tribasic
Magnesium silicate
Magnesium stearate
Magnesium sulfate
Malic acid
L-Malic acid
Manganese glycerophosphate
Manganous chloride
Manganous citrate
Manganous gluconate
Manganous hypophosphite
Manganous oxide
Manganous sulfate
Mannitol
Methyl acrylate, monomeric (packaging)
Methyl acrylate, polymeric (packaging)
Methyl Paraben
Methylcellulose
Milo Starch
Monoammonium L-glutamate
Monopotassium L-glutamate
Monosodium L-glutamate
Monostarch Phosphate
Mustard and Oil of Mustard (Brown and Yellow)
Niacin (nicotinic acid)
Niacinamide (nicotinamide)
Nickel (elemental)

TABLE G-continued

GRAS Substance

Nutmeg and Mace
Oil of Rue
Oleic acid (packaging)
Ox bile extract
D-Pantothenyl alcohol
Papain
Peanut oil (packaging)
Pectin, amidated
Pectin, high ester
Pectin, low acid
Pectinates
Pectinic acid
Perlite (filter aid)
Phosphated Distarch Phosphate
Phosphoric acid
L(+)-potassium acid tartrate
Potassium alginate
Potassium bicarbonate
Potassium carbonate
Potassium chloride
Potassium citrate
Potassium gluconate
Potassium glycerophosphate
Potassium hydroxide
Potassium hypophosphite
Potassium iodate
Potassium iodide
Potassium metabisulfite
Potassium phosphate dibasic
Potassium phosphate monobasic
Potassium phosphate tribasic
Potassium polymetaphosphate
Potassium pyrophosphate
Potassium silicate
Potassium sorbate
Potassium tripolyphosphate
Potato starch
Pregelatinized starch
Propionic acid
Propyl Gallate
Propyl Paraben
Propylene Glycol
Propylene glycol alginate
Propylene glycol monostearate
Acid hydrolyzed proteins
Enzymatically hydrolyzed protein
Pulps (packaging)
Pyridoxine
Pyridoxine hydrochloride
Red algae
Reduced iron
Reduced iron (packaging)
Rennet
Riboflavin
Riboflavin-5'-phosphate
Rice Starch
Silica aerogel
Silicon dioxides
Sodium acetate
Sodium acid pyrophosphate
Sodium alginate
Sodium aluminate (packaging)
Sodium aluminosilicate
Sodium aluminum phosphate, acidic
Sodium aluminum phosphate, basic
Sodium Benzoate
Sodium bicarbonate
Sodium bisulfite
Sodium calcium aluminosilicate
Sodium carbonate
Sodium Carboxymethyl cellulose
Sodium caseinate
Sodium chloride
Sodium citrate
Sodium diacetate
Sodium erythorbate (sodium D-isoascorbate)
Sodium ferric EDTA
Sodium ferricitropyrophosphate TABLE G-continued GRAS Substance Sodium formate (packaging)
Sodium gluconate
Sodium hexametaphosphate
Sodium hydrosulfite (packaging)
Sodium hydroxide
Sodium Hydroxide Gelatinized Starch
Sodium hypophosphite
Sodium L-ascorbate
Sodium metabisulfite
Sodium metaphosphate
Sodium oleate (packaging)
Sodium palmitate (packaging)
D- or DL- Sodium pantothenate
Sodium phosphate dibasic
Sodium phosphate monobasic
Sodium phosphate tribasic
Sodium phosphoaluminate (packaging)
L(+)-sodium potassium tartrate
Sodium propionate
Sodium pyrophosphate, tetrabasic
Sodium sesquicarbonate
Sodium silicate
Sodium sorbate
Sodium sulfite
L(+)-sodium tartrate
Sodium tetrametaphosphate
Sodium tetraphosphate
Sodium thiosulfate
Sodium trimetaphosphate
Sodium tripolyphosphate
Sorbic acid
Sorbitol
Sorbose (packaging)
Soy protein isolate
Soy sauces
Stannous Chloride
Starch Acetate
Starch Aluminum Octenyl Succinate
Starch Sodium Octenyl Succinate
Starch Sodium Succinate
Starch, Sodium Hypochlorite oxidized
Starter distillate
Stearic acid (packaging)
Stearyl citrate
Sterculia Gum (karaya gum)
Succinic acid
Succinyl Distarch Glycerol
Sucrose
Sulfamic acid (packaging)
Sulfur dioxide
Sulfuric Acid
Talc (basic magnesium silicate)
Tall oil (packaging)
Tallow (packaging)
Tannic acid (hydrolyzable gallotannins)
Tapioca Starch
L(+)-tartaric acid
Taurocholic acid
Thiamine hydrochloride
Thiamine mononitrate
Thiodipropionic acid
alpha-Tocopherol acetate
Tocopherols
Tricalcium silicate
Triethyl citrate
Urea
Vitamin A
Vitamin A acetate
Vitamin A palmitate
Vitamin B12 (cyanocobalamin)
Vitamin D2 (ergocalciferol)
Vitamin D3 (cholecalciferol)
Waxy Maize Starch
Wheat Starch
Yeast autolyzates
Zinc acetate
Zinc carbonate
Zinc chloride TABLE G-continued GRAS Substance Zinc gluconate
Zinc hydrosulfite (packaging)
Zinc oxide
Zinc sulfate A. Formulations The compounds disclosed herein can be prepared and administered in a wide variety of oral, parenteral, and topical dosage forms. Preferred embodiments of the methods described herein involve oral administration of one or more compounds described herein. The compounds described herein can additionally be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds disclosed herein can be administered transdermally. It is also envisioned that multiple routes of administration (e.g., intramuscular, oral, etc.) can be used to administer the compounds disclosed herein.

Compounds are administered in solid or liquid form as appropriate with the desired method of administration. For oral administration, the compound can be administered as a solid or a liquid for in various embodiments. For some embodiments that are administered as injections, the compound can be delivered as a liquid or in a liquid suspension.

In some oral embodiments, the compounds disclosed herein can be administered as solids, more specifically in the form of tablets, lozenges, troches, powders, granules, or capsules. In some other oral embodiments, the compounds disclosed herein can be administered as liquids more specifically as solutions, aqueous or oily suspensions, capsules, emulsions, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In powders, the carrier is a finely divided solid in a mixture with the finely divided active component. In tablets, the active component is mixed with the carrier having the necessary binding properties in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, microcrystalline cellulose, mannitol, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included.

In some embodiments, tablets contain the active ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch, alginic acid, and polymers such as Kollidon® CL, also known as crospovidone; (3) binding agents, such as starch, gelatin or acacia; and (4) lubricating agents, such as magnesium stearate, stearic acid or talc. These tablets can be uncoated or coated with a film or layer by known techniques to delay disintegration and absorption in the gastrointestinal tract and thereby provide a sustained action over a longer period. For example, a time delay material such as glyceryl monostearate or glyceryl distearate can be employed. Other examples include Eudragit® L 30 D-55, a polymer that includes copolymerized methacrylate and which prevents dissolution below pH 5.5.

In some embodiments, tablets contain the active ingredient as an amorphous solid. This can be achieved by generating an amorphous solid dispersion containing the active ingredient and at least one polymer. In some embodiments, that polymer is Kollidon® VA64 which is a vinylpyrrolidone-vinyl acetate copolymer. One of skill in the art will appreciate that a certain weight ratio of active ingredient to polymer is necessary to maintain the active ingredient in an amorphous state. This active ingredient:polymer weight ratio can range from 1:1 to upwards of 1:10. In some embodiments, an active ingredient:polymer weight ratio is 1:3. One of skill in the art will also appreciate that there are a variety of techniques available to produce an amorphous solid dispersion including holt melt extrusion and spray-dried dispersion (SDD) methods.

In certain embodiments, it can be desirable to control particle size distribution. A number of techniques, including micronization techniques, can be employed to produce a desired particle size distribution in certain embodiments of a given formulation.

Also included are solid form preparations that are intended to be converted, shortly before use, to liquid form preparations for oral administration. Such liquid forms include solutions, suspensions, and emulsions. These solutions can be of water or water/propylene glycol mixtures. These preparations can contain, in addition to the active component, one or more colorants, flavors, stabilizers, buffers, artificial and natural sweeteners, surfactants, dispersants, thickeners, solubilizing agents, and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material such as natural or synthetic gums, resins, methylcellulose, sodium carboxymethylcellulose, and other well-known suspending agents.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, polyethylene glycol, and the like. Ampoules are convenient unit dosages. The compounds discloser herein can also be incorporated into liposomes or administered via transdermal pumps or patches. Pharmaceutical admixtures suitable for use in the pharmaceutical compositions and methods disclosed herein include those described, for example, in PHARMACEUTICAL SCIENCES (17$^{th}$ Ed., Mack Pub. Co., Easton, PA) and WO 96/05409, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles including fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulations, and/or otherwise to improve the formulation. Such viscosity binding agents include, for example, polyvinyl alcohol, polyvinyl pyrrolidone, methyl cellulose, hydroxypropyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Aqueous suspensions normally contain the active materials in admixture with excipients suitable for the manufacture of the aqueous suspension. Such excipients can be (1) suspending agent such as sodium carboxymethyl cellulose, methyl cellulose, hydroxypropyl methylcellulose, sodium alginate, polyvinylpyrrolidone, gum tragacanth and gum acacia; (2) dispersing or wetting agents which can be (a) naturally occurring posphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g. Goodman and Gilman (eds.), 1990, THE PHARMACOLOGICAL BASIS FOR THERAPEUTICS (7$^{th}$ ed.).

A compound disclosed herein can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

For preparing suppositories, a low melting wax, such as a mixture of fatty acid glycerides or the aforementioned cocoa butter, is first melted and the active component is dispersed homogeneously therein, as by stirring. The molten homogeneous mixture is then poured into convenient sized molds, allowed to cool, and thereby to solidify.

For topical use, creams, ointments, jellies, solutions or suspensions, etc., containing the compounds disclosed herein are employed.

The compounds disclosed herein as used in the methods disclosed herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For in vivo application, a compound disclosed herein, can be administered parenterally by injection or gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The pharmaceutical compositions are preferably prepared and administered in dose units. For treatment of a subject, depending on activity of the compound, manner of administration, nature and severity of the disease or disorder, age and body weight of the subject, different daily doses can be used. Typically, dosages used in vitro can provide useful guidance in the amounts useful for in situ administration of the pharmaceutical composition, and animal models can be used to determine effective dosages for treatment of particular disorders.

Under certain circumstance, however, higher or lower daily doses can be appropriate. The administration of the daily dose can be carried out both by single administration in the form of an individual dose unit or else several smaller dose units and also by multiple administrations of subdivided doses at specific intervals.

Various considerations are described e.g., in Langer, 1990, *Science,* 249:1527; Goodman and Gilman's (eds.), 1990, Id., each of which is herein incorporated by reference and for all purposes. Dosages' parenteral administration of active pharmaceutical agents can be converted into corresponding dosages for oral administration by multiplying parenteral dosages by appropriate conversion factors. As to general application, dosages from in vivo animal studies can be adapted to a human equivalent dose (HED) by applying the appropriate animal scale factor to the mg/kg ratio for the given in vivo animal. An average adult human weighs about 60 kg. See e,g, GUIDANCE FOR INDUSTRY: Estimating the Maximum Safe Starting Dose in Initial Clinical Trials for Therapeutics in Adult Healthy Volunteers (FDA Guidance; July 2005)

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of thrombin, cell culture assays, and the like. Target concentrations will be those concentrations of active compound(s) that are capable of decreasing enzymatic activity as measured, for example, using the methods described.

Therapeutically effective amounts for use in humans can be determined from animal models. For example, a dose for humans can be formulated to achieve a concentration that has been found to be effective in animals. The dosage in humans can be adjusted by monitoring enzymatic inhibition and adjusting the dosage upwards or downwards, as described above.

Dosages can be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of, e.g., about 0.1 mg to about 1 mg, about 1 mg to about 10 mg, about 0.5 mg to about 20 mg per kilogram body weight, and average adult weighing 60 kilograms, with a preferred dosage range between about 0.1 mg to about 20 mg per kilogram body weight per day (from about 6.0 mg to about 1.2 g per patient per day). The amount of the compound disclosed herein that can be combined with the carrier materials to produce a single dosage will vary depending upon the host treated and the particular mode of administration. For example, a formulation intended for oral administration to humans can contain about 5 µg to 1 g of a compound disclosed herein with an appropriate and convenient amount of carrier material that can vary from 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein and not to limit the scope of the disclosure. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

General Synthesis of Pyrazole-Pyridone Compounds

General Synthetic Scheme 1 depicted below provides a general synthesis for acylated pyrazole-pyridone compounds as disclosed within. In the following General Scheme I, the terms "$R^x$", "$R^y$" and "$R^z$" are independently hydrogen, substituted or unsubstituted alkyl, substituted or unsubstituted heteroalkyl, substituted or unsubstituted cycloalkyl, substituted or unsubstituted cycloalkenyl, substituted or unsubstituted or unsubstituted heterocycloalkyl, substituted or unsubstituted heterocycloalkenyl, substituted or unsubstituted aryl, substituted or unsubstituted heteroaryl, or other groups that would apparent to those skilled in the art.

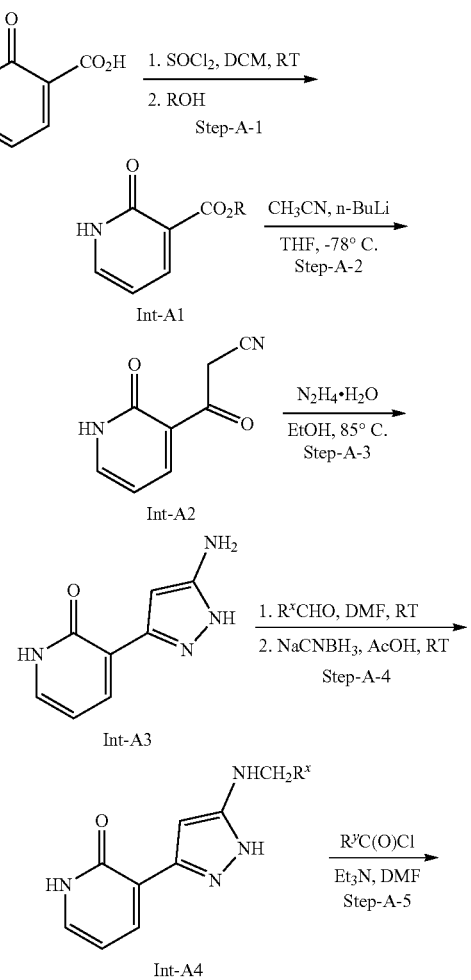

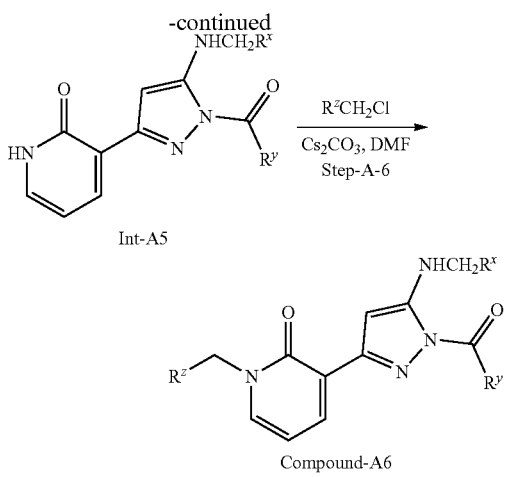

Step-A-1—Synthesis of Exemplary Int-A1

To a solution of 2-hydroxynicotinic acid (50.0 g, 0.359 moles, 1.0 equiv.) in dichloromethane (500 mL, 10 V) at 0° C. was added thionyl chloride (133.6 mL, 1.798 moles, 5.0 equiv., 2.67 V) dropwise. After 30 min tetrahydrofuran (500 mL, 10 V) was added and the reaction stirred for 14-15 hours at ambient temperature. The reaction mixture was cooled to 0° C., to it was added methanol (150 mL, 3 V) dropwise, and the mixture was stirred for a further 30 min at room temperature. The reaction mixture was concentrated under reduced pressure to obtain a solid, which was then neutralized with aqueous sodium bicarbonate (pH 7-8), and again concentrated to obtain solid product. The solid was dissolved in methanol, filtered, and the filtrate concentrated to give desired product, an exemplary Int-A1, methyl-2-oxo-1,2-dihydropyridine-3-carboxylate (45.0 g, 81.8% yield) m/z 153.99 [M+H]+ 1H NMR (DMSO-d6, 400 MHz) δ 8.051-074 (1H, q), 7.661-7.682 (1H, q), 6.259-6.292 (1H, m), 3.734 (3H, s) ppm.

Step-A-2—Synthesis of Int-A2

To a cold (−78° C.) solution of acetonitrile (8.18 mL, 0.156 moles, 1.2 equiv., 0.41 V) in tetrahydrofuran (300 mL, 15 V) was added n-BuLi (2.5M in Hexane; 62.68 mL, 0.156 moles, 1.2 equiv., 3.13 V) dropwise over a period of 60 min. After addition, the reaction was stirred for another 60 min, then to it added methyl 2-oxo-1,2-dihydropyridine-3-carboxylate (Int-A1, 20.0 g, 130 mmol, 1.0 eq) portionwise to reaction mixture and maintained −78° C. for 3 hr. The reaction was quenched with water and washed with ethyl acetate. The aqueous layer was evaporated to obtain crude product, which was suspended in methanol and stirred for 30 min at room temperature. The solid was filtered through suction and dried over high vacuum to afford Int-A2 (11.5 g, 54% yield).

Step-A-3—Synthesis of Int-A3

To a solution of Int-A2 (20.0 g, 0.123 moles, 1.0 equiv.) in isopropanol (600 mL, 30 V) and acetic acid (22.2 mL, 1.11 V) was added hydrazine monohydrate (7.40 mL, 0.148 moles, 1.2 equiv., 0.37 V) dropwise and the reaction was heated at 85° C. for 4-5 hours. After cooling, the reaction mixture was concentrated to give crude product, which was purified by column chromatography using neutral silica gel (60-120 mesh), eluting with 10-25% methanol in dichloromethane as gradient to give the desired product Int-A3 (13.25 g, 61% yield) m/z 177.06 [M+H]+ 1H NMR (DMSO-d6, 400 MHz) δ 11.831 (1H, s), 7.857-7.879 (1H, q), 7.383-7.403 (1H, q), 6.303-6.336 (1H, m), 6.048 (1H, s) 4.633 (2H, s) ppm.

Step-A-4—Synthesis of Exemplary Int-A4

To a solution of Int-A3 (10.0 g, 0.0568 mol) in dimethylformamide (100 mL, 10 V) at 10-15° C. was added acetic acid (11.2 mL, 1.12 V) dropwise, followed by 5-chlorothiophene-2-carbaldehyde (9.15 g, 0.0624 moles, 1.1 equiv.) added portionwise. The reaction was stirred for 30-45 min at room temperature. Sodium cyanoborohydride (5.35 g, 0.0851 moles, 1.5 equiv.) was added portionwise over a period of 45 min and reaction was stirred for 2 hours. After completion of reaction, the mixture was poured into ice cold water under stirring and the product was extracted with ethyl acetate. The organic layer was dried over sodium sulfate and concentrated under reduced pressure to obtain crude product, which was purified by column chromatography using neutral silica gel and product was eluted with 10-12% methanol in dichloromethane as mobile phase to yield pure desired product, an exemplary Int-A4, 3-(5-{[(5-chlorothiophen-2-yl)methyl]amino}-1H-pyrazol-3-yl)-1,2-dihydropyridin-2-one (7.3 g, 42.7% yield) m/z [M+H]+ 307.10 1H NMR (DMSO-d6, 400 MHz) δ 12.034 (1H, s), 11.815 (1H, s), 7.869-7.882 (1H, q), 7.404-7.415 (1H, d), 6.922-6.931 (1H, d), 6.862-6.871 (1H, d), 6.314-6.331 (1H, d), 6.117 (1H, s), 5.867-5.898 (1H, t), 4.348-4.363 (2H, d) ppm. One of skill will appreciate that a variety of borohydride reagents can be used in this step to achieve similar results.

Step-A-5—Synthesis of Exemplary Int-A5

To a cooled (0° C.) solution of the above exemplary Int-A4 in triethylamine (2.98 mL, 0.0215 moles, 3.0 equiv.) and dichloromethane (40 mL) was added pivaloyl chloride (0.776 g, 0.00647 moles, 0.9 equiv.) dropwise over a period of 30 minutes. The reaction was stirred for 2-3 hours by maintaining the temperature below 10° C. After completion, the reaction was diluted with ice cold water under stirring and the product was extracted with dichloromethane. The organic phase was dried over sodium sulfate and concentrated under reduced pressure. The resultant crude product was purified by column chromatography using neutral silica gel, eluting with 5-8% methanol in dichloromethane to furnish pure desired product, and exemplary Int-A5, 3-(5-{[(5-chlorothiophen-2-yl)methyl]amino}-1-(2,2-dimethylpropanoyl)-1H-pyrazol-3-yl)-1,2-dihydropyridin-2-one (0.76 g, 43.6% yield) m/z [M+H]+ 391.24 1H NMR (DMSO-d6, 400 MHz) δ 11.250 (1H, s), 8.086-8.109 (1H, q), 7.731-7.761 (1H, t), 7.484 (1H, s), 6.974-6.984 (1H, d), 6.934-6.944 (1H, d), 6.317-6.350 (1H, t), 6.213 (1H, s), 4.471-4.486 (2H, d), 1.47 (9H, s) ppm. One of skill in the art will appreciate that a variety of methods and reagents can be used to acylate the pyrazole center, such as generating an active ester.

Step-A-6—Synthesis of Exemplary Compound-A6

Exemplary Int-A5 (0.200 g, 5.1×10⁻⁶ mol) was dissolved in dimethyl formamide (5 mL, 25 V) and stirred. Cesium carbonate (0.400 g, 1.2×10⁻³ mol) was then added and stirred for 10 to 15 minutes. Then 2-bromo ethyl methyl ether (0.075 g. 8.1×10-6 mol, 1.5 equiv.) was added and the reaction further stirred at room temperature until completion as determined by TLC monitoring. The reaction mass was then diluted in excess water and extracted with ethyl acetate before being purified by column chromatography to yield exemplary Compound-A6, 3-(5-{[(5-chlorothiophen-2-yl)methyl]amino}-1-(2,2-dimethylpropanoyl)-1H-pyrazol-3-yl)-1-(2-methoxyethyl)-1,2-dihydropyridin-2-one, also listed above in Table A as Compound 7 (0.030 g, 13.2% yield) 1H NMR (DMSO-d6, 400 MHz) δ 8.094-8.071 (dd, J=7.2, 2.0 Hz, 1H), 7.757 (m, 2H), 6.984 (d, J=4 Hz, 1H), 6.945 (d, J=3.6, 1H), 6.358 (t, J=7.0 Hz, 1H), 6.215 (s, 1H), 4.479 (d, J=7.0 Hz, 2H), 4.138 (t, J=5.2, 2H), 3.598 (t, J=5.2

Hz, 2H), 3.243 (s, 3H), 1.471 (s, 9H) ppm. One of skill in the art will appreciate that potassium carbonate can be preferable over cesium carbonate in certain analogous reactions depending upon the specifics of the reagents involved.

Example 2

Specific Synthesis of Compound 1

Specific Synthesis Scheme I, depicted below, provides a specific synthesis for Compound 1, 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid.

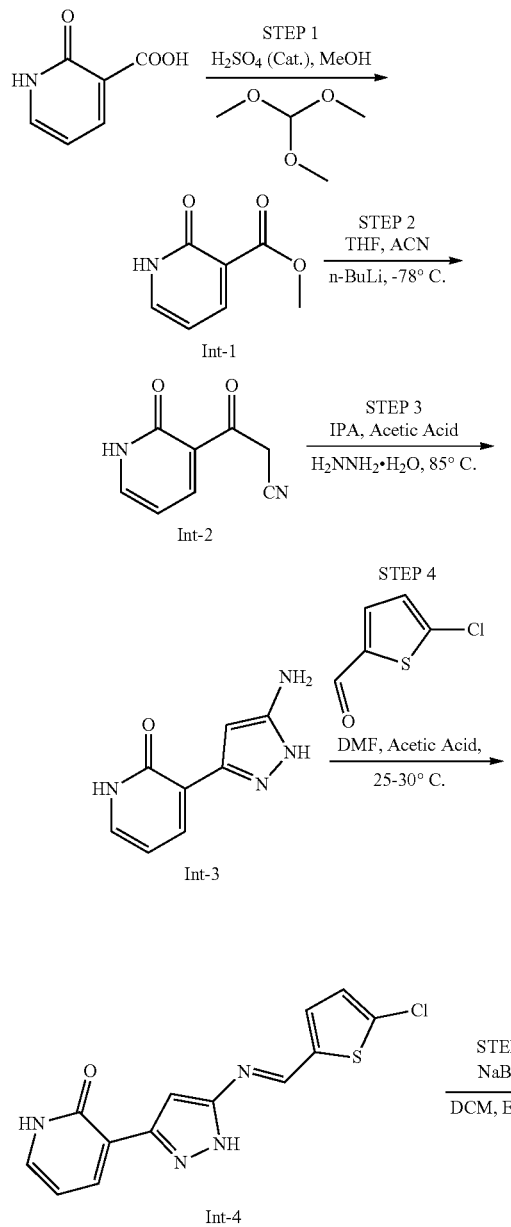

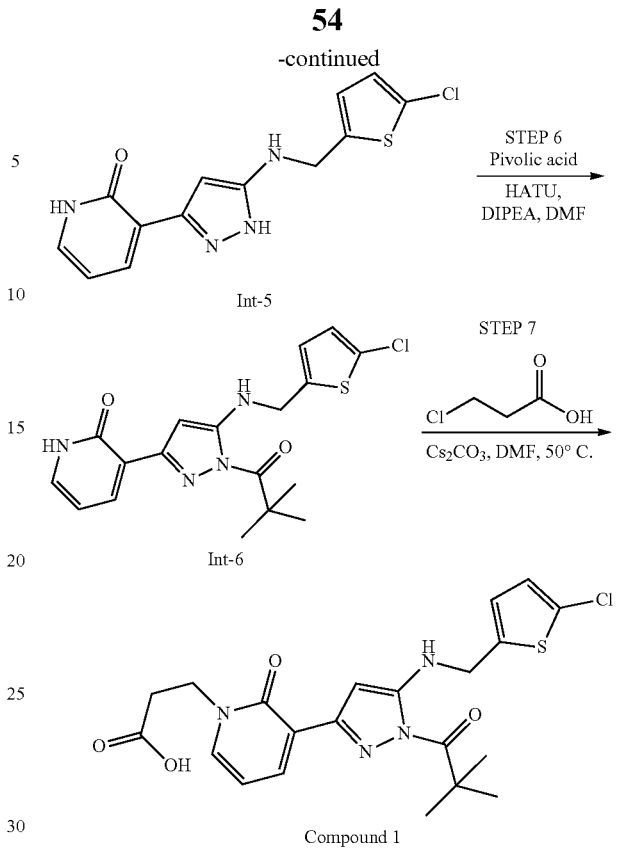

Step 1—Synthesis of Int-1

Trimethyl orthoformate (286.06 g, 2.696 mol, 1.5 equiv.) was added at 25-30° C. to a mixture of 2-hydroxynicotinic acid (250 g, 1.797 mol) in methanol (3750 mL, 15 V). The mixture was stirred for 15 minutes, after which concentrated $H_2SO_4$ (52.87 g, 0.539 mol, 0.3 equiv.) was added at 25-30° C. The mixture was then refluxed at 65-70° C. for 2 hours. After swapping the reflux condenser with a distillation apparatus, the mass was then distilled for 4 hours to constant volume to remove unreacted trimethyl orthoformate. After having cooled to 25-30° C., the reaction mixture was then slowly added to a mixture of $NaHCO_3$ (200 g, 2.381 mol, 1.32 equiv.) in MeOH (500 mL) to bring the pH to 7.0 and then stirred for 15 minutes at the same temperature. The resulting mass was filtered through Celite® and washed with MeOH (250 mL, 1 V). Next, by keeping the mass temperature below 55° C., the filtrate was distilled under vacuum until the inner volume was reduced to about 2 volumes. The mass was then diluted with toluene (1250 mL, 5 V), and again distilled down to about 2 volumes, a process called "solvent chasing" using toluene. This process was repeated until the MeOH content of the mass was less than 300. Finally, the mass was cooled to 25-30° C., diluted with toluene (750 mL, 3 V), filtered, and washed with toluene (500 mL, 2 V) before being dried at 65-70° C. under vacuum to obtain unpurified Int-1 (315 g, 76% yield). [1H NMR (DMSO-d6, 400 MHz) δ 12.107 (s, 1H), 8.056 (dd, J=6.8, 2.0 Hz, 1H), 7.663 (dd, J=6.4, 2.4 Hz, 1H), 6.269 (t, 6.8 Hz, 1H), 3.776 (s, 3H)].

Step 2—Synthesis of Int-2

A solution of n-butyllithium (549 mL, 2.5 M in hexane, 1.37 mol, 2.1 equiv.) was added dropwise to a solution of acetonitrile (71.3 mL, 1.37 mol, 2.1 equiv.) in tetrahydrofuran (4500 mL, 45 V) at −70 to −80° C. The resulting mass was then stirred for 1 hour at −70 to −80° C. Int-1 (100 g, 0.653 mol) was then added. The total mixture was stirred for an additional 3 hours at −70 to −80° C., after which, the mass was quenched with DM H$_2$O (1500 mL, 15 V) at −70 to 0° C., stirred for 10-15 minutes at 0-5° C., and diluted with ethyl acetate (2000 mL, 20 V). The mixture was then warmed to 25-30° C. and stirred for 15 minutes before the organic layer was separated. The aqueous layer was then cooled to 10-15° C. and had its pH adjusted to 2-3 with 6N aqueous HCl. The slurry was stirred for 30 minutes at 10-15° C. before being filtered, washed with DM H$_2$O (400 mL, 4 V), and dried under vacuum at 50-55° C. for 6 hours to obtain Int-2 (40.2 g, 38% yield). [1H NMR (DMSO-d6, 400 MHz) δ 8.185 (dd, J=7.6, 2.4 Hz, 1H), 7.808 (dd, J=6.0, 2.0 Hz, 1H), 6.441 (t, J=6.8 Hz, 1H), 3.716 (s, 2H)].

Step 3—Synthesis of Int-3

Acetic acid (45.6 mL, 1.14 V) was added at 25-30° C. to a mixture of Int-2 (40 g, 0.2466 mol) in isopropanol (400 mL, 10 V). The resulting mass was stirred for 10-15 minutes at the same temperature. Then hydrazine hydrate (14.81 g, 0.296 mol, 1.2 equiv.) was added to the reaction mixture whereupon it was heated to 80-85° C. and stirred for about 3 hours by which Int-2 was less than 1% by area by HPLC analysis. The resulting mass was cooled to 25-30° C., filtered, washed with isopropanol (2×40 mL), and finally vacuum dried at 50-55° C. to acquire Int-3 (36.0 g, 83.3% yield). [1H NMR (DMSO-d6, 400 MHz) δ 11.784 (s, 2H), 7.867 (dd, J=7.2, 1.6 Hz, 1H), 7.391 (dd, J=6.4, 2.0 Hz, 1H), 6.319 (t, J=6.8 Hz, 1H), 6.047 (s, 1H), 4.622 (s, 1H)].

Step 4—Synthesis of Int-4

5-Chlorothiophene-2-carbaldehyde (31.81 g, 0.2185 mol, 1.1 equiv.) was added to a mixture of Int-3 (35.0 g, 0.1986 mol) in DMF (350 mL, 10 V) at 25-30° C. and then stirred for 15 minutes. Then acetic acid (41.75 g, 0.695 mol, 1.1 equiv.) was added. The mixture was stirred for about 2 hours until Int-3 content was less than 1% by area by HPLC analysis. The resulting mass was then slowly added to DM H$_2$O (1750 mL, 50 V) at 25-30° C., filtered, washed with DM H$_2$O (350 mL, 10 V), and vacuum dried at 50-55° C. to obtain Int-4 (55.0 g, 90.9% yield).

Step 5—Synthesis of Int-5

Sodium borohydride (7.7 g, 0.2035 mol, 2 equiv.) was slowly added to a suspension of Int-4 (31.0 g, 0.1017 mol, 1 equiv.) in dichloromethane (310 mL, 10 V) and ethanol (310 mL, 10 V) at 0-5° C. The resulting mixture was then warmed to 25-30° C., stirred for 30 minutes. Then additional sodium borohydride (7.7 g, 0.20 mol, 2 equiv. and 3.85 g, 0.1018 mol, 1 equiv.) was added in two portions spaced 30 minutes apart. The mixture was then stirred for 1 hour at 25-30° C. after which the Int-4 content was less than 1% by area by HPLC analysis. The mixture was then cooled to 10-20° C., and the pH was adjusted to 7-8 using 1 N aqueous HCl (355 mL, 11.45 V). The mass was then stirred for 1 hour at a temperature of 25-30° C., after which it was filtered, washed with DM H$_2$O (155 mL, 5 V) and dried under reduced pressure at 60-65° C. for 10 hours to obtain Int-5. Using this procedure, one skilled in the art can expect chemical yields approaching 100% for this step, using the techniques and methods described herein, or techniques and methods understood to be functionally equivalent, as appreciated by those skilled in the art. [1H NMR (DMSO-d6, 400 MHz) δ 11.867 (s, 2H), 7.859 (d, J=5.6 Hz, 1H), 7.406 (d, J=4.8 Hz, 1H), 6.890 (dd, J=22.8, 3.6 Hz, 2H), 6.323 (t, J=6.8 Hz, 1H), 6.106 (s, 1H), 5.860 (t, J=6 Hz, 1H), 4.353 (d, J=6 Hz, 2H)].

Step 6—Synthesis of Int-6

HATU (46.47 g, 0.122 mol, 1.5 equiv.) was added at 25-30° C. to a solution of pivalic acid (16.64 g, 0.163 mol, 2 equiv.) in DMF (250 mL, 10 V). The mixture was then stirred for 30 minutes at 25-30° C., thereafter Int-5 (25.0 g, 0.0815 mol, 1 equiv.) was added lot-wise and stirred further for 5 minutes. Then, DIPEA (42.58 mL, 0.245 mol, 3 equiv.) was added dropwise at 25-30° C. and was stirred for an additional 1 hour at 25-30° C. The reaction mass was then cooled to 15° C., diluted with DM H$_2$O (250 mL, 10V) and then its pH was adjusted to 5.8-6.3 with 1% aqueous citric acid while keeping the mass temperature below 25° C. The resulting mass was then stirred for 30 minutes at 25-30° C., filtered, washed with DM H$_2$O (250 mL, 10 V) and dried under reduced pressure at 55-60° C. for 10 hours to obtain Int-6. Using this procedure, one skilled in the art can expect an average chemical yield of 59% for this step using the techniques and methods described herein, or techniques and methods understood to be functionally equivalent, as appreciated by those skilled in the art. [1H NMR (400 MHz, DMSO-d6) δ 11.92-11.86 (m, 1H), 8.09 (dd, J=7.0, 2.1 Hz, 1H), 7.73 (t, J=6.2 Hz, 1H), 7.48 (dd, J=6.4, 2.2 Hz, 1H), 7.00-6.90 (m, 2H), 6.33 (t, J=6.7 Hz, 1H), 6.21 (s, 1H), 4.47 (d, J=6.1 Hz, 2H), 1.47 (s, 9H)].

Step 7—Synthesis of Compound 1

Cesium carbonate (333.4 g, 1.023 mol, 4.0 equiv.) was slowly added to a suspension of Int-6 (100 g, 0.256 mol, 1.0 equiv.) in DMF (500 mL, 5 V) at 25-30° C. The mixture was stirred for 10 minutes. A solution of 3-chloropropionic acid (41.64 g, 0.384 mol, 1.5 equiv.) in DMF (250 mL, 2.5 V) was added dropwise at 25-30° C. The resulting mass was stirred for one hour, then filtered and washed twice with DMF (100 mL, 1 V). The filtrate was then slowly added to DM H$_2$O (4000 mL, 40 V) while keeping the mass temperature at 20-30° C. and stirred for 10 minutes. The pH was adjusted to 4.5 to 5.0 using 2N aqueous HCl at 20-30° C. The reaction mass was then stirred for 30 minutes, filtered, and washed twice with 200 mL of DM H$_2$O to yield compound 1. Using this procedure, one skilled in the art can expect an average chemical yield of 19%, using the techniques and methods described herein, or techniques and methods understood to be functionally equivalent, as appreciated by those skilled in the art. [1H NMR (DMSO-d6, 300 MHz) δ 12.43 (s, 1H), 8.06 (m, 1H), 7.81 (m, 1H), 7.74 (m, 1H), 6.95 (dd, J=12.0, 3.0 Hz, 2H), 6.35 (t, J=6.0 Hz, 1H), 5.74 (s, 1H), 4.46 (d, J=6.0 Hz, 2H), 4.13 (t, J=7.5 Hz, 2H), 2.69 (t. J=6.0 Hz, 2H), 1.45 (s, 9H)].

To purify the final product, ethyl acetate (400 mL, 4 V) was added to the crude wet product (216 g) and was stirred for 1 hour at 25-30° C. After removing the aqueous layer, the organic layer was then treated with charcoal (8.0 g) for 30 minutes at 25-30° C. It was then filtered through diatomaceous earth (12 g), and the earth bed subsequently was washed with ethyl acetate (120 mL). The ethyl acetate was distilled off from the filtrate until the inner volume reached approximately 150 mL (1.5 V) while keeping the mass temperature below 40° C. The mass was then cooled to 25-30° C., stirred for 30 minutes, and then seeded with pure int-5 (0.1% w/w). The slurry was cooled 0-5° C. and stirred for 1 hour. The slurry was then filtered and washed twice with pre-chilled (0-5° C.) ethyl acetate (20 mL, 0.2 V). The mass was then dried under vacuum at 25-30° C.

The product was further purified by adding n-heptane (670 mL, 10 V) dropwise to a solution of Compound 1 (67 g) in dichloromethane (670 mL, 10 V) at 25-30° C. The slurry was then stirred for 30 minutes at 25-30° C., filtered and washed with n-heptane (134 mL). The solid was then dried under vacuum at 25-30° C.

This synthesis resulted in a crystalline solid having an x-ray powder diffraction pattern comprising a selection of one, two, three, four, five, or 2θ values selected from the list consisting of 9.9° 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, each within an error range of ±0.3°, as shown in FIG. 1 as crystal Form 1. The solid was analyzed on a Bruker D8Advance X-ray Powder Diffractometer (Tube: Cu:Kα (λ=1.54179 Å), Generator: 40 kV; 40 mA, and Scan scope: 3-40 deg). One of skill in the art will appreciate that variance in XRPD plots can arise from a variety of sources. Therefore, for all XRPD plots in this disclosure, there are certain embodiments wherein the error range for each peak is ±0.0°, ±0.1°, ±0.2°, ±0.3°, ±0.4°, ±0.5°, ±0.6°, ±0.7°, ±0.8°, ±0.9°, or ±1.0°.

Example 3

Specific Synthesis of Compound 2

Specific Synthetic Scheme II, depicted below, provides a synthesis of Compound 2, 3-[3-(5-{[(5-chlorothiophen-2-yl)methyl]amino}-1H-pyrazol-3-yl)-2-oxo-1,2-dihydropyridin-1-yl]propanoic acid.

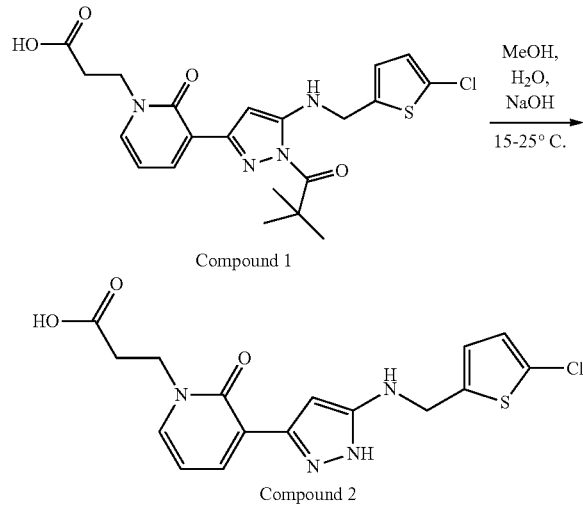

Specific Synthetic Scheme II

Compound 1

Compound 2

In its singular step, Compound 1 (1 g, 2.16 mmol) was dissolved in methanol (10 mL, 10 V), and reagent-grade water (2 mL, 2 V). Then, NaOH (431.97 mg, 10.80 mmol, 5 equiv.) was added as one portion while the mixture was at 15-25° C. The mixture was then stirred for 1 hr at 15-25° C. Ice water (10 mL, 10 V) were then added to the mixture, and its pH was subsequently adjusted to 5-6 using 6N HCl (11 mL, 11 V). The resulting solid was filtered and washed with water (10 mL, 10 V) to collect Compound 2 (0.5 g, 1.32 mmol, 61.10% yield). [1H NMR 400 MHz, DMSO-d6) δ 7.839 (m, 1H), 7.704 (m, 1H), 6.860 (dd, 2H), 6.334 (t, 1H), 6.107 (s, 1H), 4.331 (s, 2H), 4.141 (t, 2H), 2.695 (t, 2H)]

Example 4

Polymorphs

Some embodiments are crystalline solids of compound 1, that can exist as a number of polymorphs. In one example, the solid material has the polymorph as depicted in FIG. 1. To convert a quantity of compound 1 into the polymorph of FIG. 1, the following procedure was performed. Compound 1 was dissolved in THF/EA (4 V/10 V) mixture at 30° C. and filtered. The solution was than cooled to 5° C. and seeded with a seed crystal from the synthesis process described above in Specific Synthetic Scheme I. The mixture is then stirred at 5° C. for three hours thereafter 15 V of n-heptane are added over 10 hours at 5° C. Following that, 21 V of n-heptane are further added for 5 hours at 5° C. and was then stirred for an additional 22-24 hours at 5° C. before collection of the solid. When examined by XRPD, the resulting spectrum showed peaks including those at 9.9°, 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, each within an error range of ±0.3°, as shown in FIG. 1 as crystal Form 1. The XRPD data was taken on a Bruker D8Advance X-ray Powder Diffractometer (Tube: Cu:Kα (λ=1.54179 Å), Generator: 40 kV; 40 mA, Scan scope: 3-40 deg, Sample rotation speed: 15 rpm, and Scanning rate: 10 deg/min). Thermogravimetric analysis (TGA) and differential scanning calorimetry (DSC) data are reported below in Table H.

In another embodiment, compound 1 was a crystalline solid with an XRPD spectrum showing peaks at 4.9°, 9.7°, 14.4°, 16.0°, 16.5°, 17.0°, 18.2°, 18.5°, 19.2°, 19.7°, 20.2°, 22.8°, 23.3°, 24.0°, 24.5°, and 24.8° each within an error range of +0.3° as shown in FIG. 2 as crystal Form 2. In this embodiment, compound 1 (35 mg) were mixed with isopropyl alcohol (0.5 mL) and slurried protected from light at room temperature and 500 rpm for 2 days. The solid was then separated via an Eppendorf 5418 centrifuge at 14000 rpm for 10 minutes and then dried under vacuum at room temperature over three days. The sample was then checked by XRPD, TGA, and DSC. The XRPD data was taken on a Bruker D8Advance X-ray Powder Diffractometer (Tube: Cu:Kα (λ=1.54179 Å), Generator: 40 kV; 40 mA, Scan scope: 3-40 deg, Sample rotation speed: 15 rpm, and Scanning rate: 10 deg/min). TGA and DSC data are reported below in Table H.

In another embodiment, compound 1 was a crystalline solid with an XRPD spectrum showing peaks at 8.6°, 9.5° 11.8°, 12.4°, 12.9°, 14.2°, 15.2°, 15.5°, 16.5°, 17.2°, 18.8°, 19.1°, 20.1°, 20.9°, and 22.9° within at least ±0.3° as shown in FIG. 3 as crystal Form 3. In this embodiment, compound 1 (15.6 mg) were mixed with a 1:1 ethanol:water mixture (0.3 mL) and slurried at 40° C. and 500 rpm for one day. The solid was then separated via an Eppendorf 5418 centrifuge at 14000 rpm for 10 minutes and then dried under vacuum at room temperature over three days. The sample was then checked by XRPD, TGA, and DSC. The XRPD data was taken on a Bruker D8Advance X-ray Powder Diffractometer (Tube: Cu:Kα (λ=1.54179 Å), Generator: 40 kV; 40 mA, Scan scope: 3-40 deg, Sample rotation speed: 15 rpm, and Scanning rate: 10 deg/min). TGA and DSC data are reported below in Table H.

Example 5

Salt Synthesis

Some embodiments include compound 1 as a salt with an appropriate counter-ion. In some embodiments, this counterion is tris(hydroxymethyl)aminomethane, hereafter referred to as "Tris." To generate a tris salt of compound 1, 320 mg of compound 1 was placed in a glass vial and dissolved in 10.7 mL of acetone. The vial was then sonicated for a few moments to generate a hazy suspension. This suspension was then centrifuged at 10,000 rpm for 5 minutes in an Xiangyi H1650 centrifuge, and 1.67 mL of the supernatant was isolated from the rest of the pellet and volume. To this 1.67 mL portion of supernatant, 0.059 mL of Tris (2N solution in water) was added to generate a molar ratio of 1:1.1 of compound 1:Tris. The mixture was then stirred for 24 hours at room temperature. The resulting suspension was then centrifuged for 10 minutes at 10,000 rpm in an Eppendorf Centrifuge 5418 to separate out the solid materials which were then dried in a Boxun DZF-6050 Vacuum Oven at 40° C. overnight. The solid was then analyzed on a Bruker D8Advance X-ray Powder Diffractometer (Tube: Cu:Kα (λ=1.54179 Å), Generator: 40 kV; 40 mA, Scan scope: 3-40 deg, Sample rotation speed: 15 rpm, and Scanning rate: 10 deg/min). FIG. 4 shows the resulting XRPD spectrum. In this embodiment, compound 1 exists in a crystalline form having an x-ray powder diffraction pattern comprising a selection of one, two, three, four, five, or more 2θ values selected from the list consisting of 6.8°, 10.0°, 13.0°, 15.1°, 16.0°, 16.5°, 18.0°, 18.4°, 19.8°, 20.5°, 20.8°, 21.2°, 21.5°, 22.8°, 23.3°, and 25.9°, each within an error range of ±0.3° as shown in FIG. 4 as crystal Form 4. TGA and DSC data are reported below in Table H.

One of skill in the art will appreciate that similar salts can be made by a similar process utilizing the appropriate amount of another counterion to generate a molar ratio of 1:1.1 compound 1:counterion in the mixture. Examples of alternative counterions include sodium, potassium, calcium, L-arginine, L-lysine, and meglumine. The resulting salt can be collected by similar means as what is expressed above.

TABLE H

| Form | TGA Weight Loss % | TGA Temp. Range (° C.) | DSC Onset Temp. (° C.) | DSC Specific Enthalpy (J/g) |
|---|---|---|---|---|
| 1 | 0.06% | 35.91-120.40 | 147.06 | Endo 101.47 |
| 2 | 0.34% | 22.21-120.00 | 158.85 | Endo 53.97 |
|  | 3.20% | 120.00-156.59 |  |  |
| 3 | 2.03% | 28.61-98.54 | 87.70 | Endo 73.80 |
|  |  |  | 116.36 | Endo 19.16 |
| 4 | 0.39% | 28.00-100.00 | 162.2 | Endo 89.10 |

Thermal gravimetric analysis (TGA) data was measured on a TA Q5000IR using samples with mass between 0.5 and 5.0 mg in an open platinum pan that was heated from room temperature to 250° C. at a rate of 10° C./min.

Differential scanning calorimetry (DSC) data was measured on a TA Q2000 using samples with mass between 0.5 and 1.0 mg in a crimped aluminum pan with a small hole in the lid that was heated from room temperature to 250° C. at a rate of 10° C./min.

Example 6

Metabolites of Compound 1

Certain metabolites of Compound 1 have been detected from various in vivo and in vitro studies. These compounds include the compounds listed below in Table I. Compounds 10, 13, and 14 are proposed metabolites.

TABLE I

| Compound No. | IUPAC | Structure |
|---|---|---|
| 2 | 3-[3-(5-{[(5-chlorothiophen-2-yl)methyl]amino}-1H-pyrazol-3-yl)-2-oxo-1,2-dihydropyridin-1-yl]propanoic acid | 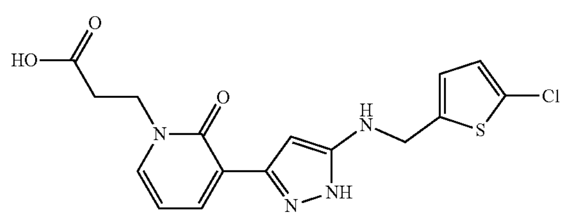 [SMILES: O=C(O)CCn1cccc(-c2cc(NCc3ccc(Cl)s3)[nH]n2)c1=O] |
| 10 | 3-[3-(5-{[(5-chlorothiophen-2-yl)methyl]amino}-1-(3-hydroxy-2,2-dimethylpropanoyl)-1H-pyrazol-3-yl)-2-oxo-1,2-dihydropyridin-1-yl]propanoic acid | 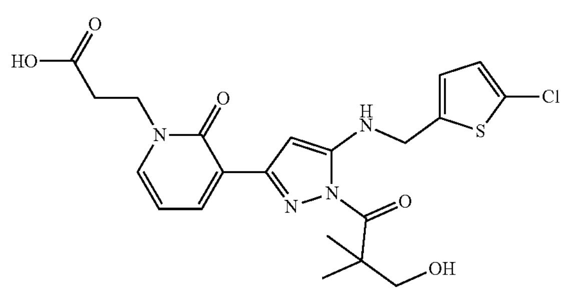 [SMILES: CC(C)(CO)C(=O)n1nc(-c2cccn(CCC(=O)O)c2=O)cc1NCc1ccc(Cl)s1] |
| 13 | 3-[3-(5-{[(5-chloro-1-oxo-1lambda4-thiophen-2-yl)methyl]amino}-1-(2,2-dimethylpropanoyl)-1H-pyrazol-3-yl)-2-oxo-1,2-dihydropyridin-1-yl]propanoic acid | 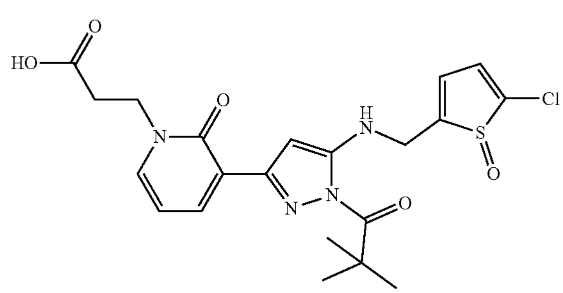 [SMILES: CC(C)(C)C(=O)n1nc(-c2cccn(CCC(=O)O)c2=O)cc1NCC1=CC=C(Cl)S1=O] |

TABLE I-continued

| Compound No. | IUPAC | Structure |
|---|---|---|
| 14 | (2S,3S,4S,5R,6S)-6-({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)-3,4,5-trihydroxyoxane-2-carboxylic acid | 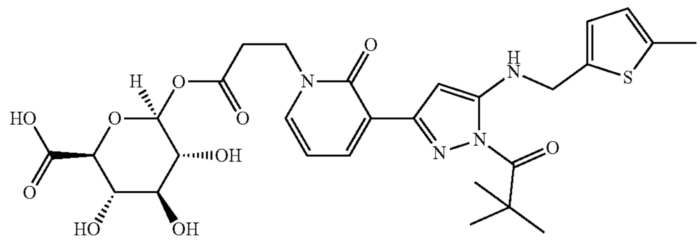 [SMILES: Cc1ccc(CNc2cc(-c3cccn(CCC(=O)O[C@@H]4O[C@H](C(=O)O)[C@@H](O)[C@H](O)[C@H]4O)c3=O)nn2C(=O)C(C)(C)C)s1] |

15

Metabolites of Compound 1 have a variety of uses as appreciated by those of skill in the art. Certain metabolites, such as Compound 10, have biological activity (see Table B above). Metabolites of Compound 1 can also be useful as pharmacokinetic indicators of Compound 1 in biological assays and organisms including human patients.

Example 7

Pharmaceutical Compositions

Example 7a—Amorphous Solid Dispersion of Compound 1

A pharmaceutical composition containing Compound 1 as an amorphous solid in an amorphous solid dispersion with the polymer Kollidon® VA64, a vinylpyrrolidone-vinyl acetate copolymer, was prepared. The amorphous solid dispersion contained a 1:3 weight ratio of Compound 1 to Kollidon® VA64 and was prepared by a spray-dried dispersion (SDD) technique as appreciated by those skilled in the art using THF as the solvent and with the following process parameters: Nozzle Temperature=40° C.; Process Temperature=80° C., Nozzle Gas Flow Rate=4.0 kg/hr, Chamber Gas Flow Rate=35.0 kg/hr, Spray Rate=32 g/min. The material was then dried for 48 hr in a convection oven at 50° C. followed by another 18 hr at 60° C. One of skill in the art will appreciate that a variety of weight ratios of Compound 1 to Kollidon® VA64 can be used to achieve the desired amorphous state of Compound 1 in the amorphous solid dispersion.

Example 7b—Tablet Formulation of Compound 1 as an Amorphous Solid Dispersion

Compound 1, as an amorphous solid dispersion as described in the above example 7a, was formulated into a tablet. One skilled in the art will appreciate that embodiments of the invention can comprise a variety of pharmaceutically acceptable excipients, which would be known to those skilled in the art. For example, these excipients can include disintegrants such as crospovidone, fillers such as microcrystalline cellulose and mannitol, and lubricants or glidants such as magnesium stearate and/or talc. In the present example, the tablet was prepared to include the following ingredients in the below listed weight ratios in comparison to the total mass of the tablet.

TABLE J

| Ingredient | wt/wt % |
|---|---|
| Amorphous Solid Dispersion of Compound 1 | 50.00 |
| Crospovidone (Kollidon® CL) | 10.00 |
| Magnesium Stearate | 2.00 |
| Microcrystalline Cellulose | 19.00 |
| Mannitol | 18.00 |
| Talc | 1.00 |

In one preparation, the tablet had a total mass of 180 mg±9 mg. In another preparation, the tablet had a total mass of 1000 mg±50 mg.

In further embodiments, the tablets are coated with an exterior film or layer called an enteric coating. This layer, which comprises a polymer and/or other materials, can provide additional properties, such as resistance to dissolution in an environment below pH 5.5. In some embodiments, the polymer is a copolymer that comprises copolymerized methacrylate. In the present example, the polymer of this exterior film or layer was Eudragit® L 30 D-55.

Example 7c—Process of Making the Tablet of Example 7b

The process used for making the tablet of Example 7b as disclosed above is provided herein. First, an amorphous solid dispersion of Compound 1 was produced via the spray-dried dispersion technique utilizing a 1:3 weight ratio of Compound 1 to Kollidon® VA64, as described above in Example 7a.

Next, this amorphous solid dispersion was mixed with intragranular raw materials. In one embodiment of the invention, these materials can comprise at least one disintegrant and at least one lubricant. In some embodiments, the intragranular raw materials additionally comprise at least one filler. In the present example, the disintegrants included crospovidone (Kollidon® CL), and the lubricant was magnesium stearate, and the intragranular raw materials additionally comprised microcrystalline cellulose (Avicel® PH 101) and mannitol (Partek® M 100). One of skill in the art will appreciate that these intragranular ingredients can be de-lumped by use of a mesh screen. In the present example, the fillers, disintegrants, and the amorphous solid dispersion were de-lumped and blended for ten minutes before de-lumped lubricant was added to the mixture and blended for an additional three minutes.

This blended mixture of intragranular materials and amorphous solid dispersion can then be compacted and subsequently milled. In the present example, a roller compactor was used exerting 5 kN of force, and the mass was milled into ribbons with a 1,000 μm screen at 20 rpm. These compacted ribbons were then further ground down into granules, by methods appreciated by those of skill in the art.

In one embodiment, the above mixing was performed under dry conditions, and the granulating performed was dry granulation. In the present example, dry mixing and dry granulation was used.

Next, the dry granules of the above step were further mixed with extragranular raw materials. In one embodiment of the invention, these materials comprise at least one disintegrant and at least one lubricant and/or glidants and at least one filler. In the present example, the disintegrants included crospovidone (Kollidon® CL), and the lubricants and/or glidants included magnesium stearate and talc, and the extragranular raw materials additionally included microcrystalline cellulose and mannitol (Partek® M 100). One of skill in the art will appreciate that these extragranular ingredients can be de-lumped by use of a mesh screen. In the present example, de-lumped filler(s) and disintegrant(s) were first blended with the granules for ten minutes before de-lumped lubricant(s) and/or glidant(s) were added to the mixture and blended for an additional three minutes to generate a final mixture.

This final mixture was then compressed into tablets of a desired shape and size having the properties shown in Table J.

In some preparations, the mass of the tablets was 180 mg±9 mg, while in other preparations, the tablets were 1000 mg±50 mg in mass. One of skill in the art will appreciate that the parameters of the compression step, such as press speed and compression force, varies depending on the desired shape, size, mass, and other properties of the chosen embodiment of the tablet.

In the present example, the distribution of ingredients between the intragranular and extragranular portions as a weight percentage of total tablet weight were as depicted below in Table K.

TABLE K

| Ingredient | Intragranular wt/wt % | Extragranular wt/wt % | Total wt/wt % |
|---|---|---|---|
| Amorphous solid dispersion of Compound 1 | 50 | 0 | 50 |
| Crospovidone (Kollidon ® CL) | 5 | 5 | 10 |
| Magnesium stearate | 1 | 1 | 2 |
| Microcrystalline cellulose | 9.5 | 9.5 | 19 |
| Mannitol | 9 | 9 | 18 |
| Talc | 0 | 1 | 1 |

Finally, the compressed tablets were coated with a film or layer. In some embodiments, this exterior layer comprises a polymer and conveys additional properties on the tablet, such as preventing dissolution in a pH below 5.5. In some embodiments, the polymer contains polymerized methacrylic acid-ethyl acrylate. In the present example, this polymer was Eudragit® L 30 D-55. Furthermore, this polymer was used in mixture that was 57% Eudragit® L 30 D-44, 14.6% plasacryl HTP20, and 28.4% water. One of skill in the art will appreciate that evaporation techniques may well reduce the final water composition due to water evaporation. One of skill in the art will appreciate that there are a variety of techniques available to coat the tablets with this exterior layer. In some embodiments a pan coating technique is employed.

Embodiments of the disclosure can be described in view of the following clauses:

1. A compound according to Structure I.

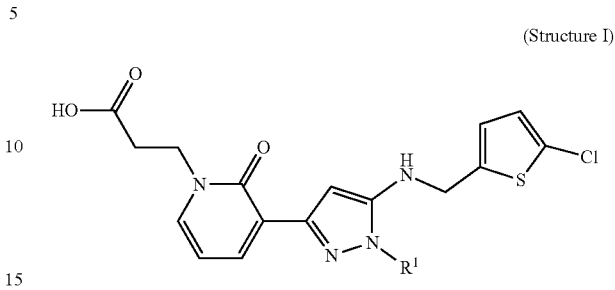

(Structure I)

or pharmaceutically acceptable salt, solvate, or cocrystal thereof, wherein $R^1$ is selected from the group consisting of hydrogen and pivaloyl.

2. A prodrug of the compound according to clause 1 according to the general Structure II:

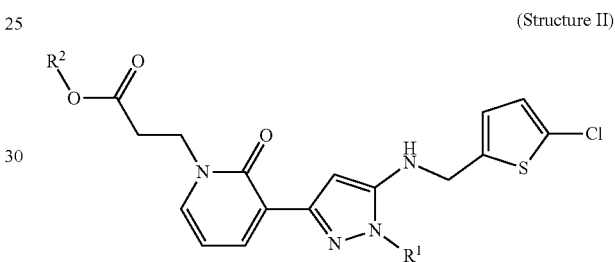

(Structure II)

or a pharmaceutically acceptable salt, solvate, or cocrystal thereof;

wherein $R^1$ is selected from the group consisting of hydrogen and pivaloyl; and wherein $R^2$ is selected from the group consisting of substituted or unsubstituted alkyl and substituted or unsubstituted heteroalkyl.

3. The prodrug of clause 2, wherein $R^2$ is selected from the following groups:

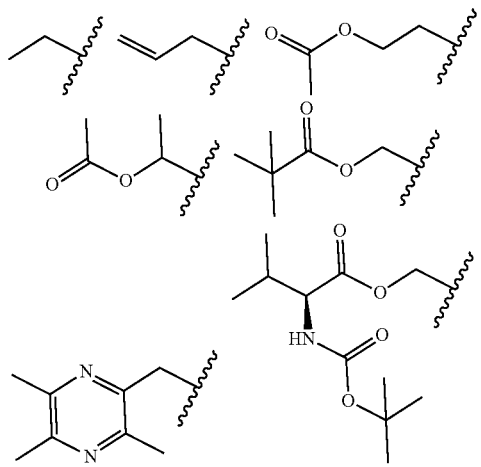

4. The compound according to clauses 1, wherein $R^1$ is pivaloyl, as Compound 1:

(Compound 1)

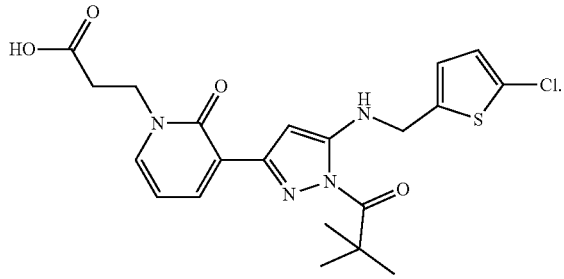

5. The compound according to clause 1 or 4, wherein the compound is in crystalline form.

6. The compound according to clause 5, wherein the crystalline form has an x-ray powder diffraction pattern comprising at least five 2θ values selected from the group consisting of 9.9°, 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, wherein each of the at least five 2θ values is within an error range of ±0.3°.

7. The compound according to clause 5, wherein the crystalline form has an x-ray powder diffraction pattern comprising at least five 2θ values selected from the group consisting of 4.9°, 9.7°, 14.4°, 16.0°, 16.5°, 17.0°, 18.2°, 18.5°, 19.2°, 19.7°, 20.2°, 22.8°, 23.3°, 24.0°, 24.5°, and 24.8°, wherein each of the at least five 2θ values is within an error range of ±0.3°.

8. The compound according to clause 5, wherein the crystalline form has an x-ray powder diffraction pattern comprising at least five 2θ values selected from the group consisting of 8.6°, 9.5°, 11.8°, 12.4°, 12.9°, 14.2°, 15.2°, 15.5°, 16.5°, 17.2°, 18.8°, 19.1°, 20.1°, 20.9°, and 22.9°, wherein each of the at least five 2θ values is within an error range of ±0.3°.

9. The compound according to any of clauses 1 or 4-8, wherein $R^1$ is hydrogen, as Compound 2:

(Compound 2)

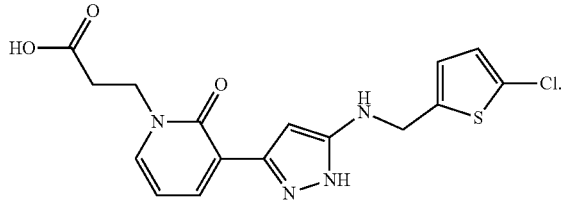

10. The compound according to any of clauses 1 or 4-9, wherein said compound is in the form of a pharmaceutically acceptable salt.

11. The compound according to clause 10, wherein the pharmaceutically acceptable salt has a counter-ion selected from the group consisting of sodium, potassium, calcium, L-arginine, L-lysine, meglumine, and tris(hydroxymethyl) aminomethane.

12. The compound according to clause 11, wherein said counter-ion is tris(hydroxymethyl)aminomethane.

13. The compound according to any of clauses 1 or 4-12, wherein $R^1$ is pivaloyl.

14. The compound according to clause 13, wherein the compound is in crystalline form having an x-ray powder diffraction pattern comprising at least five 2θ values selected from the group consisting of 6.8°, 10.0°, 13.0°, 15.1°, 16.0°, 16.5°, 18.0°, 18.4°, 19.8°, 20.5°, 20.8°, 21.2°, 21.5°, 22.8°, 23.3°, 25.9°, wherein each of the at least five 2θ values is within an error range of ±0.3°.

15. A compound or prodrug according to any of the preceding clauses, selected from the group consisting of:
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid;
3-[3-(5-{[(5-chlorothiophen-2-yl)methyl]amino}-1H-pyrazol-3-yl)-2-oxo-1,2-dihydropyridin-1-yl]propanoic acid;
2-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]acetic acid;
4-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]butanoic acid;
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]-2,2-difluoropropanoic acid;
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propenamide;
1-(2-amino-2-methylpropyl)-3-(5-{[(5-chlorothiophen-2-yl)methyl]amino}-1-(furan-3-carbonyl)-1H-pyrazol-3-yl)-1,2-dihydropyridin-2-one;
3-[3-(5-{[(5-chlorothiophen-2-yl)methyl]amino}-1-(3-hydroxy-2,2-dimethylpropanoyl)-1H-pyrazol-3-yl)-2-oxo-1,2-dihydropyridin-1-yl]propanoic acid;
3-[3-(5-{[(5-chlorothiophen-2-yl)methyl]amino}-1-(2,2-dimethylbutanoyl)-1H-pyrazol-3-yl)-2-oxo-1,2-dihydropyridin-1-yl]propanoic acid;
3-[3-(5-{[(5-chlorothiophen-2-yl)methyl]amino}-1-(furan-3-carbonyl)-1H-pyrazol-3-yl)-2-oxo-1,2-dihydropyridin-1-yl]propanoic acid;
3-[3-(5-{[(5-chloro-1-oxo-1lambda4-thiophen-2-yl)methyl]amino}-1-(2,2-dimethylpropanoyl)-1H-pyrazol-3-yl)-2-oxo-1,2-dihydropyridin-1-yl]propanoic acid;
(2S,3S,4S,5R,6S)-6-({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)-3,4,5-trihydroxyoxane-2-carboxylic acid;
ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;
prop-2-en-1-yl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate; 2-(acetyloxy)ethyl;
3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;
1-(acetyloxy)ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;
({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl 2,2-dimethylpropanoate;
(3,5,6-trimethylpyrazin-2-yl)methyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;
({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl (2S)-2-{[(tert-butoxy)carbonyl]amino}-3-methylbutanoate;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl](2H4)propanoic acid;

3-{3-[5-({[5-chloro(3,4-2H2)thiophen-2-yl](2H2)methyl}amino)-1-(2,2-dimethylpropanoyl)-1H-pyrazol-3-yl]-2-oxo-1,2-dihydropyridin-1-yl}propanoic acid; and 3-[3-(5-{[(5-chlorothiophen-2-yl)(2H2)methyl]amino}-1-(2,2-dimethylpropanoyl)-1H-pyrazol-3-yl)-2-oxo-1,2-dihydropyridin-1-yl]propanoic acid.

16. A pharmaceutical composition comprising a compound or prodrug according to any of clauses 1 through 15, or a pharmaceutically acceptable salt, solvate, or cocrystal thereof, and a pharmaceutically acceptable excipient.

17. A method for treating and/or preventing a disease or disorder in a subject, comprising administering a compound or prodrug according to any of clauses 1 to 15 or a pharmaceutical composition according to clause 16 to a subject in need thereof in an amount effective to treat or prevent said disease or disorder.

18. The method according to clause 17, wherein said disease or disorder is a thrombotic disease or disorder and/or involves a blood clot thrombus or the potential formation of a blood clot thrombus.

19. The method according to clause 18, wherein said thrombotic disease or disorder comprises acute coronary syndrome, thromboembolism, and/or thrombosis.

20. The method according to clause 19, wherein said thromboembolism comprises venous thromboembolism, arterial thromboembolism, and/or cardiogenic thromboembolism.

21. The method according to clause 20, wherein said venous thromboembolism comprises deep vein thrombosis and/or pulmonary embolism.

22. The method according to clause 21, wherein said deep vein thrombosis and/or pulmonary embolism occurs following a medical procedure.

23. The method according to any of clauses 18-22, wherein said thrombotic disease or disorder involves dysfunctional coagulation or disseminated intravascular coagulation.

24. The method according to clause 23, wherein the subject is undergoing percutaneous coronary intervention (PCI).

25. The method according to any of clauses 18-24, wherein said thrombotic disease or disorder involves a blood clot thrombus or the potential formation of a blood clot thrombus and further involves stroke and/or one or more transient ischemic attacks (TIA).

26. The method according to clause 25, wherein said thrombotic disease or disorder involving a blood clot thrombus or the potential formation of a blood clot thrombus further involves stroke and wherein the subject has non-valvular atrial fibrillation.

27. The method according to any of clauses 18-26, wherein said thrombotic disease or disorder involving a blood clot thrombus or the potential formation of a blood clot thrombus further involves pulmonary hypertension.

28. The method according to clause 27, wherein said pulmonary hypertension is caused by one or more left heart disorder and/or chronic thromboembolic disease.

29. The method according to clause 27, wherein said pulmonary hypertension is associated with one or more lung disease, including pulmonary fibrosis (idiopathic or otherwise), and/or hypoxia.

30. The method according to any of clauses 17-29, wherein said disease or disorder comprises fibrosis, Alzheimer's Disease, multiple sclerosis, pain, cancer, inflammation, and/or Type I diabetes mellitus.

31. The method according to any of clauses 17-30, wherein said disease or disorder involves recurrent cardiac events after myocardial infarction.

32. The method according to any of clauses 20-31, wherein said venous thromboembolism is associated with formation of a thrombus within a vein associated with one or more acquired or inherited risk factors and/or embolism of peripheral veins caused by a detached thrombus.

33. The method according to clause 32, wherein said one or more risk factors comprise a previous venous thromboembolism.

34. The method according to any of clauses 20-33, wherein said cardiogenic thromboembolism is due to formation of a thrombus in the heart associated with cardiac arrhythmia, heart valve defect, prosthetic heart valves or heart disease, and/or embolism of peripheral arteries caused by a detached thrombus.

35. The method according to clause 34, wherein said detached thrombus is in the brain (ischemic stroke).

36. The method according to clause 35, wherein said detached thrombus causes a transient ischemic attack (TIA).

37. The method according to any of clauses 34-36, wherein said cardiogenic thromboembolism is due to non-valvular atrial fibrillation.

38. The method according to any of clauses 19-37, wherein said thrombosis is arterial thrombosis.

39. The method according to clause 38, wherein said arterial thrombosis is due to one or more underlying atherosclerotic processes in the arteries.

40. The method according to clause 39, wherein said one or more underlying atherosclerotic processes in the arteries obstruct or occlude an artery, cause myocardial ischemia (angina pectoris, acute coronary syndrome), cause myocardial infarction, obstruct or occlude a peripheral artery (ischemic peripheral artery disease), and/or obstruct or occlude an artery after a procedure on a blood vessel (reocclusion or restenosis after transluminal coronary angioplasty, reocclusion or restenosis after percutaneous transluminal angioplasty of periphery arteries).

41. The method according to any of clauses 17-40, wherein said treatment or prevention comprises an adjunct therapy.

42. The method according to clause 41, wherein the subject has myocardial infarction, and said adjunct therapy is in conjunction with thrombolytic therapy.

43. The method according to clause 41 or 42, wherein the subject has unstable angina pectoris, thrombosis, and/or heparin-induced thrombocytopenia, and said adjunct therapy is in combination with antiplatelet therapy.

44. The method according to any of clauses 41-43, wherein the subject has non-valvular atrial fibrillation, and said adjunct therapy is in conjunction with one or more other therapies.

45. The method according to any of clauses 41-45, wherein the subject has at least one of coronary artery disease and heart failure, and wherein said adjunct therapy is in combination with antiplatelet therapy.

46. The method according to clause 45, wherein the subject further has valvular or non-valvular atrial fibrillation.

47. The method according to any of clauses 41-46, wherein the subject has valvular or non-valvular atrial fibrillation and is undergoing percutaneous coronary intervention with a stent, and wherein said adjunct therapy is in combination with antiplatelet therapy.

48. A tablet comprising a pharmaceutical composition comprising Compound 1 according to clause 4.

49. The tablet according to clause 48, wherein Compound 1 exists as an amorphous solid in an amorphous solid dispersion.

50. The tablet according to clause 49, wherein said amorphous solid dispersion comprises a first polymer.

51. The tablet according to clause 50, wherein said first polymer is a vinylpyrrolidone-vinyl acetate copolymer.

52. The tablet according to clause 51, wherein Compound 1 and said first polymer are present in a weight ratio of 1:3.

53. The tablet according to any of clauses 48-52, further comprising at least one disintegrant.

54. The tablet according to clause 53, wherein said disintegrant comprises crospovidone.

55. The tablet according to any of clauses 48-54, further comprising at least one filler.

56. The tablet according to clause 55, wherein said filler comprises microcrystalline cellulose or mannitol.

57. The tablet according to any of clauses 48-56, further comprising at least one lubricant or glidant.

58. The tablet according to clause 57, wherein said lubricant or glidant comprises magnesium stearate or talc.

59. The tablet according to any of clauses 48-58, further comprising an exterior layer or film.

60. The tablet according to clause 59, wherein said exterior layer or film comprises at least a second polymer.

61. The tablet according to clause 60, wherein said second polymer prevents dissolution of said tablet below pH 5.5.

62. The tablet according to clause 60 or 61, wherein said second polymer comprises Eudragit® L 30 D-55.

63. The tablet according to any of clauses 59-62, wherein said exterior layer or film comprises 57% Eudragit® L 30 D-55, 14.6 Plasacryl® HTP20, and 28.4% water.

64. The tablet according to any of clauses 59-63, wherein said second polymer comprises a methacrylic acid-ethyl acrylate copolymer.

65. The tablet according to any of clauses 48-64, wherein said amorphous solid dispersion comprises 50% of the tablet by weight.

66. The tablet according to any of clauses 48-65, further comprising an exterior layer of a second polymer, and wherein the tablet without said exterior layer is 50% by weight said amorphous solid dispersion, 10% by weight crospovidone, 2% by weight magnesium stearate, 19% by weight microcrystalline cellulose, 18% by weight mannitol, and 1% by weight talc.

67. The tablet according to clause 66, wherein the second polymer comprises Eudragit® L 30 D-55.

68. The tablet according to clause 66 or 67, wherein said tablet without said exterior layer has a total mass of 180 mg±9 mg.

69. The tablet according to clause 66 or 67, wherein said tablet without said exterior layer has a total mass of 1000 mg±50 mg.

70. A tablet comprising a pharmaceutical composition comprising a prodrug having general Structure II according to clause 2.

71. A process of manufacturing a tablet having the pharmaceutical composition of any of clauses 48-69, the process comprising:
(1) producing an amorphous solid dispersion of Compound 1;
(2) granulating said amorphous solid dispersion of step (1) with intragranular raw materials in dry conditions;
(3) blending said granules of step (2) with extragranular raw materials to form a final mixture;
(4) compressing said final mixture of step (3) into a tablet; and
(5) coating said tablet of step (4) with a film or layer.

72. The process of clause 71, the process further comprising:
(1) producing an amorphous solid dispersion of Compound 1 using a spray-dry dispersion (SDD) technique;
(2) mixing said amorphous solid dispersion of step (1) with intragranular raw materials comprising at least one disintegrant and at least one lubricant;
(3) dry granulating said mixture of step (2), wherein said granulation process comprises using a roller compactor to produce compacted ribbons, wherein said compacted ribbons are subsequently milled into granules;
(4) blending the granules of step (3) with delumped extragranular raw materials comprising a disintegrant and a lubricant;
(5) compressing the blend of step (4) into a tablet; and
(6) coating said tablet of step (5) with a film or layer.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. The numerical values presented in some embodiments of the invention may contain certain errors necessarily resulting from the standard deviation found in their respective testing measurements.

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the invention. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A compound according to Structure I:

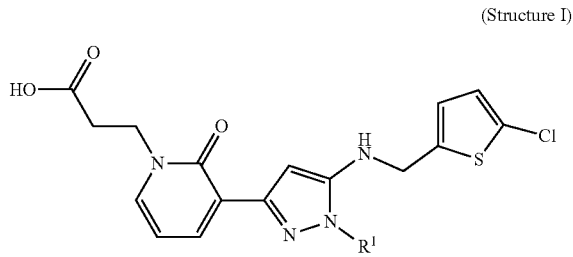

(Structure I)

or a pharmaceutically acceptable salt, solvate, or cocrystal thereof, wherein $R^1$ is selected from the group consisting of hydrogen and pivaloyl.

2. A prodrug of the compound according to claim 1 according to the general Structure II:

(Structure II)

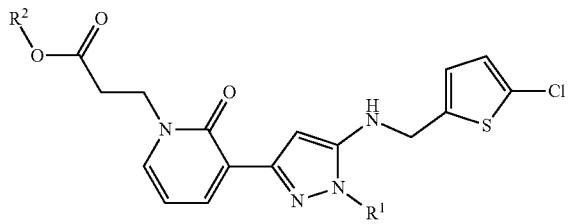

or a pharmaceutically acceptable salt, solvate, or cocrystal thereof;

wherein $R^1$ is selected from the group consisting of hydrogen and pivaloyl; and wherein $R^2$ is selected from the group consisting of substituted or unsubstituted alkyl and substituted or unsubstituted heteroalkyl.

3. The prodrug of claim 2, wherein $R^2$ is selected from the following group:

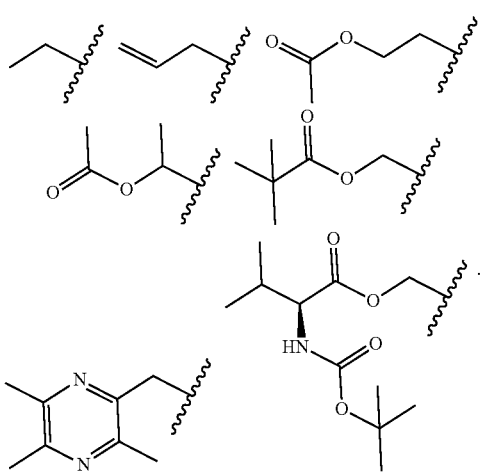

4. The compound according to claim 1, wherein $R^1$ is pivaloyl, as Compound 1:

(Compound 1)

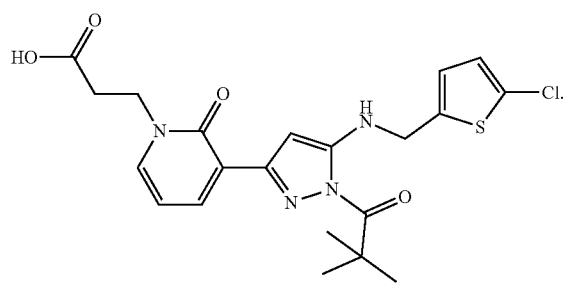

5. The compound according to claim 4, wherein the compound is in crystalline form.

6. The compound according to claim 5, wherein the crystalline form has an x-ray powder diffraction pattern comprising at least five 2θ values selected from the group consisting of 9.9°, 12.3°, 12.6°, 14.7°, 15.0°, 16.7°, 17.0°, 17.7°, 18.4°, 18.7°, 19.7°, 20.3°, 22.1°, 22.5°, 23.2°, and 24.7°, wherein each of the at least five 2θ values is within an error range of ±0.3°.

7. The compound according to claim 5, wherein the crystalline form has an x-ray powder diffraction pattern comprising at least five 2θ values selected from the group consisting of 4.9°, 9.7°, 14.4°, 16.0°, 16.5°, 17.0°, 18.2°, 18.5°, 19.2°, 19.7°, 20.2°, 22.8°, 23.3°, 24.0°, 24.5°, and 24.8°, wherein each of the at least five 2θ values is within an error range of ±0.3°.

8. The compound according to claim 5, wherein the crystalline form has an x-ray powder diffraction pattern comprising at least five 2θ values selected from the group consisting of 8.6°, 9.5°, 11.8°, 12.4°, 12.9°, 14.2°, 15.2°, 15.5°, 16.5°, 17.2°, 18.8°, 19.1°, 20.1°, 20.9°, and 22.9°, wherein each of the at least five 2θ values is within an error range of ±0.3°.

9. The compound according to claim 1, wherein $R^1$ is hydrogen, as Compound 2:

(Compound 2)

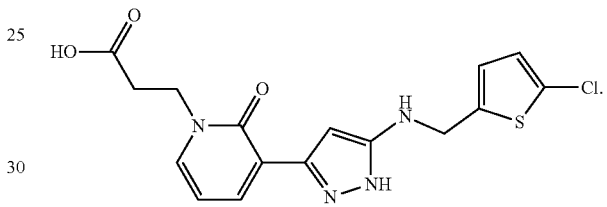

10. The compound according to claim 1, wherein said compound is in the form of a pharmaceutically acceptable salt.

11. The compound according to claim 10, wherein the pharmaceutically acceptable salt has a counter-ion selected from the group consisting of sodium, potassium, calcium, L-arginine, L-lysine, meglumine, and tris(hydroxymethyl) aminomethane.

12. The compound according to claim 11, wherein said counter-ion is tris(hydroxymethyl)aminomethane and wherein $R^1$ is pivaloyl.

13. The compound according to claim 12, wherein said counter-ion is tris(hydroxymethyl)aminomethane and wherein $R^1$ is pivaloyl, and wherein the compound is in crystalline form having an x-ray powder diffraction pattern comprising at least five 2θ values selected from the group consisting of 6.8°, 10.0°, 13.0°, 15.1°, 16.0°, 16.5°, 18.0°, 18.4°, 19.8°, 20.5°, 20.8°, 21.2°, 21.5°, 22.8°, 23.3°, and 25.9°, wherein each of the at least five 2θ values is within an error range of ±0.3°.

14. A compound or prodrug according to claim 1, selected from the group consisting of:
- 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoic acid;
- 3-[3-(5-{[(5-chlorothiophen-2-yl)methyl]amino}-1H-pyrazol-3-yl)-2-oxo-1,2-dihydropyridin-1-yl]propanoic acid;
- 2-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]acetic acid;
- 4-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]butanoic acid;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]-2,2-difluoropropanoic acid;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propenamide;

1-(2-amino-2-methylpropyl)-3-(5-{[(5-chlorothiophen-2-yl)methyl]amino}-1-(furan-3-carbonyl)-1H-pyrazol-3-yl)-1,2-dihydropyridin-2-one;

3-[3-(5-{[(5-chlorothiophen-2-yl)methyl]amino}-1-(3-hydroxy-2,2-dimethylpropanoyl)-1H-pyrazol-3-yl)-2-oxo-1,2-dihydropyridin-1-yl]propanoic acid;

3-[3-(5-{[(5-chlorothiophen-2-yl)methyl]amino}-1-(2,2-dimethylbutanoyl)-1H-pyrazol-3-yl)-2-oxo-1,2-dihydropyridin-1-yl]propanoic acid;

3-[3-(5-{[(5-chlorothiophen-2-yl)methyl]amino}-1-(furan-3-carbonyl)-1H-pyrazol-3-yl)-2-oxo-1,2-dihydropyridin-1-yl]propanoic acid;

3-[3-(5-{[(5-chloro-1-oxo-1lambda4-thiophen-2-yl)methyl]amino}-1-(2,2-dimethylpropanoyl)-1H-pyrazol-3-yl)-2-oxo-1,2-dihydropyridin-1-yl]propanoic acid;

(2S,3S,4S,5R,6S)-6-({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)-3,4,5-trihydroxyoxane-2-carboxylic acid;

ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

prop-2-en-1-yl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate; 2-(acetyloxy)ethyl;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

1-(acetyloxy)ethyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl 2,2-dimethylpropanoate;

(3,5,6-trimethylpyrazin-2-yl)methyl 3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoate;

({3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl]propanoyl}oxy)methyl (2S)-2-{[(tert-butoxy)carbonyl]amino}-3-methylbutanoate;

3-[3-(5-{[(5-chlorothiophen-2-yl)methyl]amino}-1-(2,2-dimethylpropanoyl)-1H-pyrazol-3-yl)-2-oxo-1,2-dihydropyridin-1-yl](2H4)propanoic acid;

3-{3-[5-({[5-chloro(3,4-2H2)thiophen-2-yl](2H2)methyl}amino)-1-(2,2-dimethylpropanoyl)-1H-pyrazol-3-yl]-2-oxo-1,2-dihydropyridin-1-yl}propanoic acid; and 3-[3-(5-{[(5-chlorothiophen-2-yl)(2H2)methyl]amino}-1-(2,2-dimethylpropanoyl)-1H-pyrazol-3-yl)-2-oxo-1,2-dihydropyridin-1-yl]propanoic acid.

15. A pharmaceutical composition comprising a compound or prodrug according to claim 1, or a pharmaceutically acceptable salt, solvate, or cocrystal thereof, and a pharmaceutically acceptable excipient.

16. A tablet comprising a pharmaceutical composition comprising Compound 1 according to claim 4.

17. The tablet according to claim 16, wherein Compound 1 exists as an amorphous solid in an amorphous solid dispersion.

18. The tablet according to claim 17, wherein said amorphous solid dispersion comprises a first polymer, wherein said first polymer is a vinylpyrrolidone-vinyl acetate copolymer.

19. The tablet according to claim 18, wherein Compound 1 and said first polymer are present in a weight ratio of 1:3.

20. The tablet according to claim 17, further comprising at least one disintegrant, and/or at least one filler, and/or at least one lubricant or glidant, and/or an exterior layer or film.

* * * * *